United States Patent [19]

Achard et al.

[11] Patent Number: 5,739,351
[45] Date of Patent: Apr. 14, 1998

[54] PERHYDROISOINDOLE DERIVATIVES AS SUBSTANCE P ANTAGONISTS

[75] Inventors: Daniel Achard, Thiais; Jean-François Peyronel, Palaiseau; Michel Tabart, Paris, all of France

[73] Assignee: Rhône-Poulenc Rorer S.A., Antony, France

[21] Appl. No.: 849,177
[22] PCT Filed: Nov. 29, 1995
[86] PCT No.: PCT/FR95/01577
§ 371 Date: May 30, 1997
§ 102(e) Date: May 30, 1997
[87] PCT Pub. No.: WO96/16939
PCT Pub. Date: Jun. 6, 1996

[30] Foreign Application Priority Data

Nov. 30, 1994 [FR] France .................................. 94 14345

[51] Int. Cl.[6] .......................... C07D 209/44; A61K 31/40
[52] U.S. Cl. ............................................ 548/465; 514/414
[58] Field of Search ................................. 548/452, 455, 548/465, 278.1; 514/414

[56] References Cited

U.S. PATENT DOCUMENTS 5,451,601  9/1995  Archard et al. .......................... 514/416

*Primary Examiner*—C. Warren Ivy
*Assistant Examiner*—Charanjit S. Aulakh
*Attorney, Agent, or Firm*—Finnegan, Henderson, Farabow, Garrett & Dunner, L.L.P.

[57] ABSTRACT

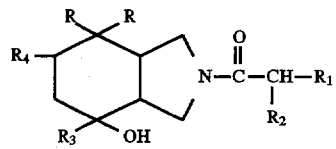

(I)

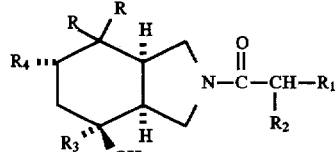

(Ia)

New perhydroinsoindole having the general formula (I) wherein $R_1$ is optionally substituted phenyl or is cyclohexadienyl, naphtyl, indenyl or mono or polycyclic heterocyclyl, saturated or unsaturated 5 to 9C and optionally substituted, $R_2$ is H or halogen, OH, alkyl, amino, aminoalkyl, alkylaminoalkyl, dialkylaminoalkyl, alkyloxy, alkylthio, acyloxy, carboxy, alkyloxycarbonyl, dialkylaminoalcyloxycarbonyl, benzyloxycarbonyl, amino or acylamino, $R_3$ is phenyl optionally substituted in position -2 by a radical alkyl or alkyloxy 1 or 2C or by OH or F, or disubstituted by $CF_3$, and $R_4$ is an alkyl radical containing 1 or 2C substituted by halogen or CN, $N_3$ or —NHCN, and the radicals R which are similar or different represent H, alkyl or phenyl, in their isomer forms having the structure (Ia) or mixtures thereof, optionally their salts when they exist and preparation thereof. The new derivatives of the invention are particularly useful as antagonists of substance P.

8 Claims, No Drawings

PERHYDROISOINDOLE DERIVATIVES AS SUBSTANCE P ANTAGONISTS

This application is a 371 of PCT/FR95/015777 which is now published as WO 95/16939 on Jun. 6, 1996.

The present invention relates to novel perhydroisoindole derivatives of general formula:

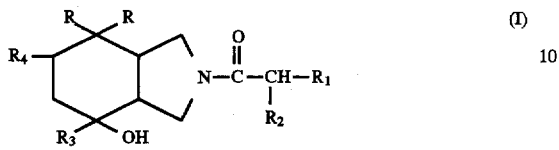

in which R, $R_1$, $R_2$, $R_3$ and $R_4$ are defined as below, and to their salts when they exist, which antagonize the effects of substance P and are, as a result, particularly advantageous in the therapeutic fields in which this substance is known to be involved.

European Patent Application EP 429 366 and the International Application WO 93 21155, both incorporated herein by reference, have described substance P antagonists of structure:

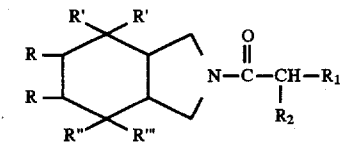

in which the symbols R are hydrogen or together form a bond, the symbols R' are optionally substituted. phenyl radicals, the symbols R" and R"' together form an oxo radical, or else one represents an optionally substituted phenyl radical and the other represents a hydroxyl radical, and the symbols $R_1$ and $R_2$ represent various substituents. Some of these products display little activity in binding tests using human lymphoblast cells in culture.

American U.S. Pat. No. 4,042,707 incorporated herein by reference, has described products derived from isoindole, of general formula:

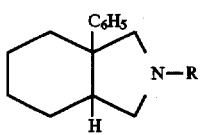

having an opiate activity. These products have no activity towards substance P.

In the general formula (I):

the symbol $R_1$ represents a phenyl radical which is optionally substituted with one or more halogen atoms or hydroxyl radicals, alkyl radicals which may be optionally substituted (with halogen atoms or with amino, alkylamino or dialkylamino radicals), alkyloxy or alkylthio radicals which may be optionally substituted [with hydroxyl, amino, alkylamino or dialkylamino radicals which are optionally substituted (with phenyl, hydroxyl or amino radicals), or dialkylamino radicals in which the alkyl moieties form, with the nitrogen atom to which they are attached, a 5- to 6-membered heterocycle which can contain another heteroatom chosen from oxygen, sulphur and nitrogen, which is optionally substituted with an alkyl, hydroxyl or hydroxyalkyl radical)], or substituted with amino radicals or with alkylamino or dialkylamino radicals in which the alkyl moieties can form, together with the nitrogen atom to which they are attached, a heterocycle as defined above, or represents a cyclohexadienyl, naphthyl or indenyl radical or a saturated or unsaturated, mono- or polycyclic heterocyclic radical containing 5 to 9 carbon atoms and one or more heteroatoms chosen from oxygen, nitrogen and sulphur, and optionally substituted with a halogen atom or with an alkyl or alkyloxy radical, the symbol $R_2$ represents a hydrogen or halogen atom or a hydroxyl, alkyl, amino, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl or acylamino radical, the symbol $R_3$ represents a phenyl radical which is optionally substituted in position 2 with an alkyl or alkyloxy radical containing 1 or 2 carbon atoms, a hydroxyl radical or a fluorine atom, or is disubstituted with trifluoromethyl radicals, and the symbol $R_4$ represents an alkyl radical containing 1 or 2 carbon atoms which is substituted with a halogen atom or with a cyano, azido or cyanamido radical, and the symbols R are identical or different and represent a hydrogen atom or an alkyl or phenyl radical.

It is understood that the abovementioned alkyl or acyl radicals contain (unless mentioned otherwise) 1 to 4 carbon atoms in a straight or branched chain.

When $R_1$ or $R_4$ contains a halogen atom, the latter can be chosen from chlorine, bromine, fluorine and iodine.

When $R_1$ represents a saturated or unsaturated, mono- or polycyclic heterocyclic radical it may, by way of example, be chosen from thienyl, furyl, pyridyl, dithiinyl, indolyl, isoindolyl, benzothienyl, thiazolyl, isothiazolyl, oxazolyl, imidazolyl, pyrrolyl, triazolyl, thiadiazolyl, quinolyl, isoquinolyl and naphthyridinyl.

When $R_1$ represents phenyl which is substituted with a chain carrying a heterocycle, the latter may be chosen from pyrrolidinyl, morpholino, piperidyl, tetrahydropyridyl, piperazinyl and thiomorpholino.

Moreover, the products of general formula (I) have different stereoisomeric forms, and it is understood that the racemic forms and the stereoisomeric forms of structure:

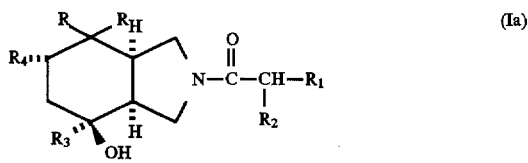

and their mixtures are within the scope of the present invention. Moreover, when the symbol $R_2$ is other than a hydrogen atom, the substituted chain on the isoindole has a chiral centre, and it is understood that the (R) and (S) stereoisomeric forms and their mixtures form part of the present invention.

According to the invention, the perhydroisoindole derivatives of general formula (I) can be obtained by reacting the acid of general formula:

or a reactive derivative of this acid in which $R_1$ and $R_2$ are defined as above with an isoindole derivative of general formula:

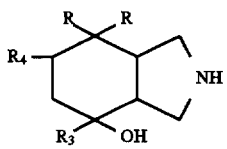

(III)

in which the symbols R, R$_3$ and R$_4$ are defined as above and then, when R$_4$ is an azidoalkyl radical, optionally converting this radical into a cyanoaminoalkyl radical.

It is understood that the amino, alkylamino or carboxyl radicals which are present in R$_1$ and/or R$_2$ are preferably protected beforehand. Protection can be afforded by any compatible group whose installation and elimination do not affect the remainder of the molecule. Protection is carried out in particular in accordance with the methods described by T. W. Greene, Protective Groups in Organic Synthesis, A. Wiley—Interscience Publication (1981) or by Mc Omie, Protective Groups in Organic Chemistry, Plenum Press (1973), both incorporated herein by reference.

By way of example, the amino or alkylamino groups can be protected by methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl or acetyl radicals or the benzyloxycarbonyl radical or its substituted derivatives;

the acid groups can be protected by methyl, ethyl, t-butyl, allyl, benzyl, substituted benzyl or benzhydryl radicals.

In addition, when the products of general formula (II) carry hydroxyl radicals, it is preferable to protect this radical beforehand. Protection is carried out in accordance with the usual methods, for example by an acetyl, trialkylsilyl or benzyl radical, in the form of a carbonate by a radical —COORa in which Ra is an alkyl or benzyl radical, or in carbonyl or carboxyl derivative form.

It is also understood that the stereochemistry of the isoindole derivative of general formula (III) is similar to that described above for the derivatives of General formula (I).

When a reactive derivative of the acid of general formula (II) is subjected to condensation, this reaction is advantageously carried out by means: of the acid chloride, anhydride, a mixed anhydride or a reactive ester in which the ester residue is a succinimido, optionally substituted 1-benzotriazolyl, 4-nitrophenyl, 2,4-dinitrophenyl, pentachlorophenyl or phthalimido radical.

The reaction is generally carried out at a temperature of between −40° and +40° C. in an organic solvent such as a chlorinated solvent (dichloromethane, dichloroethane or chloroform, for example), a hydrocarbon (toluene, for example), an ether (tetrahydrofuran or dioxane, for example), an ester (ethyl acetate, for example), an amide (dimethylacetamide or dimethylformamide, for example), or a ketone (acetone, for example) or in a mixture of these solvents in the presence of an acid acceptor such as a nitrogen-containing organic base such as, for example, pyridine, dimethylaminopyridine, N-methylmorpholine or a trialkylamine (especially triethylamine or diisopropylethylamine) or such as an epoxide (propylene oxide, for example). It is also possible to work in the presence of a condensing agent such as a carbodiimide [for example dicyclohexylcarbodiimide or 1-(3-dimethylaminopropyl)-3-ethylcarbodiimide], N,N'-carbonyldiimidazole or 2-ethoxy-1-ethoxycarbonyl-1,2-dihydroquinoline or else in an aqueous-organic medium in the presence of an alkaline condensing agent such as sodium bicarbonate.

In the variant in which a perhydroisoindole derivative of general formula (I) is obtained for which R$_4$ is an azidoalkyl radical and in which it is desired to obtain a perhydroisoindole derivative for which R$_4$ is a cyanoaminoalkyl radical, conversion is effected via the intermediate of the corresponding aminoalkyl derivative, which is obtained by reduction of the perhydroisoindole of general formula (I) for which R$_4$ is azidoalkyl, followed by treatment of the aminoalkyl derivative by the action of a cyanogen halide.

The preparation of the amine is generally carried out by hydrogenation in the presence of palladium or palladium hydroxide on charcoal in an organic solvent such as an alcohol (for example ethanol), an amide (for example dimethylformamide) or an ether (for example tetrahydrofuran) at a temperature of between 20° and 80° C.

The reaction of the cyanogen halide is carried out in a solvent such as an ether (for example tetrahydrofuran), an aromatic solvent (for example toluene) or an alcohol (for example ethanol) at a temperature of between 0° and 50° C. It is advantageously carried out using cyanogen bromide.

According to the invention, the isoindole derivatives of general formula (I) can also be obtained from a perhydroisoindole derivative of general formula:

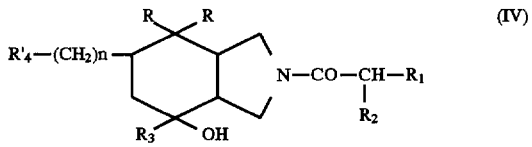

(IV)

in which the symbols R, R$_1$, R$_2$ and R$_3$ are defined as above, R'$_4$ represents a sulphonyloxy radical and n represents 1 or 2 by the action of an alkali metal cyanide, sodium azide or an alkali metal halide in order to obtain the derivative for which R$_4$ is, respectively, cyanoalkyl, azidoalkyl or haloalkyl, followed if desired by conversion of the product obtained for which R$_4$ is azidoalkyl into a product for which R$_4$ is a cyanoaminoalkyl, or else if desired by conversion of the product obtained for which R$_4$ is haloalkyl into a product of general formula (I) for which R$_4$ is cyanoalkyl or azidoalkyl.

By way of example, the radical R'$_4$ can be p-toluenesulphonyloxy or methanesulphonyloxy.

When it is desired to obtain the isoindole derivative of general formula (I) for which R$_4$ carries a cyano substituent, the reaction is carried out in particular by the action of potassium cyanide or sodium cyanide in an organic solvent such as, in particular, dimethyl sulphoxide at a temperature of between. 20° and 80° C.

When it is desired to obtain the isoindole derivative of general formula (I) for which R$_4$ carries an azido substituent, the reaction is carried out by the action of sodium azide in an organic solvent such as an amide (dimethylformamide or dimethylacetamide, for example) at a temperature of between 10° and 50° C.

When it is desired to obtain the isoindole derivative of general formula (I) for which R$_4$ carries a halogen substituent, the reaction is carried out by the action of an alkali metal halide such as, for example, lithium bromide, lithium chloride, potassium fluoride or potassium iodide, etc., in a solvent such as an alcohol (ethanol or methanol, etc.), a glycol (ethylene glycol or diethylene glycol, etc.), a ketone (acetone, etc.), an ether (tetrahydrofuran, etc.) or a mixture of solvents at a temperature of between 20° C. and the reflux temperature of the reaction mixture.

When it is desired to obtain the isoindole derivative of general formula (I) for which R$_4$ carries a cyano or azido substituent by passing through the intermediate stage of the isoindole derivative of general formula (I) for which $R_4$ carries a halogen substituent, the reaction is carried out under conditions similar to those for the preparation of the cyanoalkyl or azidoalkyl derivatives from the corresponding sulphonyloxyalkyl derivative.

When it is desired to obtain the isoindole derivative of general formula (I) for which $R_4$ carries a cyanoamino substituent, from the isoindole derivative of general formula (I) for which $R_4$ carries an azido substituent, the reaction is carried out as described above as an operation subsequent to the process of condensation of the derivatives of general formulae (II) and (III).

The acids of general formula (II) can be prepared in accordance with the methods described below in the examples, in accordance with the methods described in the patent applications EP 429 366 or WO 93 21155 or by analogy with these methods.

The isoindole derivative of general formula (III) can be obtained from the perhydroisoindole derivative of general formula:

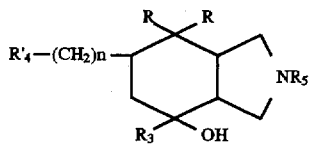

in which the symbols R, $R_3$, $R'_4$ and n are defined as above and $R_5$ is a protecting radical, by analogy with the process for the preparation of perhydroisoindole derivatives of general formula (I) from a derivative of general formula (IV), followed by elimination of the protecting radical $R_5$.

The protecting radical $R_5$ can be any amino-protecting group which is compatible with the reaction and whose installation and elimination do not adversely affect the remainder of the molecule. Groups which may be mentioned by way of example are optionally substituted alkyloxycarbonyl, benzyloxycarbonyl or benzyl or the groups allyl, formyl, chloroacetyl, trichloroacetyl, trifluoroacetyl, vinyloxycarbonyl, allyloxycarbonyl, phenoxycarbonyl, 1-chloroethoxycarbonyl or chlorocarbonyl.

The reaction is carried out under conditions identical with those described above for the preparation of the derivatives of general formula (I). The subsequent elimination of the radical $R_5$ is carried out in accordance with known methods which do not adversely affect the remainder of the molecule, and, in particular, in accordance with the methods described by T. W. Greene, Protective Groups in Organic Synthesis, A Wiley—Interscience Publication (1981), or by McOmie, Protective Groups in Organic Chemistry, Plenum Press (1973), both incorporated herein by reference.

The perhydroisoindole derivative of general formula (V) can be obtained by reacting an organometallic compound of general formula:

$R_3$—M (VI)

in which $R_3$ is defined as above and M represents lithium or a radical MgX or $CeX_2$ in which X is a halogen atom with the corresponding perhydroisoindolone derivative of general formula:

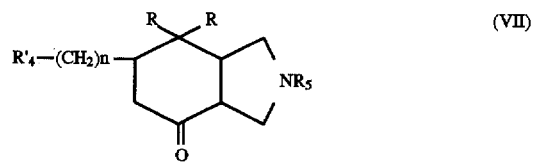

in which R, $R'_4$, $R_5$ and n are defined as above.

The reaction is carried out in an anhydrous medium under the conditions which are usual for reaction of organometallic compounds with a ketone and which do not affect the remainder of the molecule. In particular, it is carried out in an anhydrous ether (for example tetrahydrofuran or ethyl ether) optionally in the presence of anhydrous cerium chloride at a temperature of between −78° and 30° C.

The perhydroisoindole derivative of general formula (VII) can be obtained by reacting a sulphonic acid derivative of structure $R'_4$—H with the hydroxy derivative of general formula:

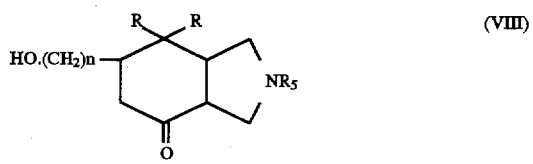

in which R, $R_5$ and n are defined as above.

The reaction is carried out in particular by the action of the acid chloride in an organic solvent such as a halide (dichloromethane, dichloroethane or chloroform, for example) in the presence of a nitrogen-containing organic base like those mentioned above (for example triethylamine).

The perhydroisoindolone derivative of general formula (VIII) can be prepared as described below in the examples and by analogy with the methods described in the Patent Application EP 429 366. It is understood that, in accordance with the nature of the desired substituents R, it will be appropriate to start from the suitably substituted cyclohexenone.

The perhydroisoindole derivative of general formula (IV) can be obtained by reacting a sulphonic acid derivative of structure $R'_4$—H with the corresponding hydroxy derivative of general formula:

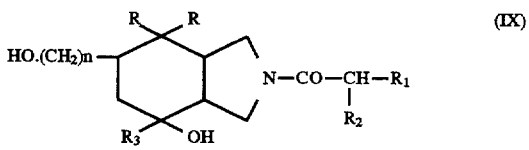

in which R, $R_1$, $R_2$, $R_3$ and n are defined as above.

The reaction is carried out under conditions similar to those described for obtaining the perhydroisoindolone of general formula (VII).

The perhydroisoindole derivative of general formula (IX) can be obtained by reacting an acid of general formula (II) or a reactive derivative thereof with the perhydroisoindole derivative of general formula:

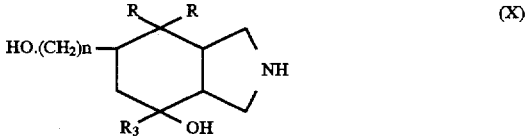

in which R, $R_3$ and n are defined as above.

The reaction is carried out by analogy with the preparation of the products according to the invention by condensing an acid of general formula (II) with a perhydroisoindole derivative of general formula (III).

The perhydroisoindole derivative of general formula (X) can be obtained by reacting an organometallic compound of general formula (VI) with the corresponding perhydroisoindolone derivative of general formula (VIII) in which the hydroxyl radical in position 6 can be protected beforehand, working in analogy to the preparation of the derivatives of general formula (V), followed by the elimination of the protecting radicals according to the usual methods which do not adversely affect the remainder of the molecule.

The reaction is carried out under the conditions described for obtaining the product of general formula (V) and as described in more detail in the examples. If appropriate, the protection of the hydroxyl radical in position 6 can be carried out according to known methods.

It is understood that the perhydroisoindole derivatives of general formula (I), (III), (IV), (V), (VII), (VIII), (IX) or (X) can have a variety of stereoisomeric forms. When it is desired to obtain an enantiomer of a product of general formula (I), separation is carried out for example at the stage of the derivative of general formula (I) or at the stage of an intermediate of general formula (VII) or (VIII) which carries an oxo radical in position 4. It can also be carried out at the stage of the derivative of general formula (III), (IV), (V), (IX) or (X). The separation is carried out according to any known method which is compatible with the molecule.

By way of example, the separation may be carried out by preparing an optically active salt by the action of L(+)- or D(−)-mandelic acid or dibenzoyltartaric acid or ditoluoyltartaric acid followed by separation of the isomers by crystallization. The desired isomer is liberated from its salt in a basic medium.

Another possible alternative, if appropriate, is to prepare the compound directly from an enantiomer of the initial cyclohexenone.

The perhydroisoindole derivatives of general formula (III) are novel products which are also within the scope of the present invention.

The isoindole derivatives of general formula (I) can be purified, where appropriate, by physical methods such as crystallization or chromatography.

Where appropriate, the novel derivatives of general formula (I) for which the symbols $R_1$ and/or $R_2$ contain amino or alkylamino substituents, or the intermediates of General formulae (III) and (X) may be converted to addition salts with acids. Examples which may be mentioned of addition salts with pharmaceutically acceptable acids are the salts formed with mineral acids (hydrochlorides, hydrobromides, sulphates, nitrates, phosphates) or with organic acids (succinates, fumarates, tartrates, acetates, propionates, maleares, citrates, methanesulphonates, p-toluenesulphonates or isethionates, or with substitution derivatives of these compounds).

The novel isoindole derivatives of general formula (I) can also, where appropriate, when $R_2$ represents a carboxyl radical, be converted to metal salts or to addition salts with a nitrogen-containing base, according to methods known per se. These salts can be obtained by the action of a metal base (for example an alkali metal or alkaline-earth metal base), ammonia or an amine on a product according to the invention, in an appropriate solvent such as an alcohol, an ether or water, or by exchange reaction with a salt of an organic acid. The salt formed precipitates after optional concentration of the solution and is separated by filtration, decantation or freeze-drying. Examples which can be mentioned of pharmaceutically acceptable salts are the salts with alkali metals (sodium, potassium, lithium) or with alkaline-earth metals (magnesium, calcium), the ammonium salt, salts of nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhyldrylamine, quinine, choline, arginine, lysine, leucine, dibenzylamine).

The novel isoindole derivatives according to the present invention which antagonize the effects of substance P may find an application in the fields of analgesia, inflammation, asthma, allergies, in the central nervous system, in the cardiovascular system, as antispasmodics, as antiemetics, or in the immune system, as well as in the field of the stimulation of lachrymal secretions.

In fact, the products according to the invention display an affinity for substance P receptors at concentrations of between 0.3 and 1000 nM in accordance with the techniques adapted from D. G. Payan et al., J. of immunology, 133(6), 3260–5 (1984): Stereospecific receptors for substance P on cultured human IM-9 lymphoblasts, and from Mc Pherson et al., J. Pharmacol. Meth., 14, 213 (1985): Analysis of radioligand binding experiments, both incorporated herein by reference.

It has in addition been demonstrated that what is involved is a substance P antagonist effect, using various products. In the technique described by S. Rosell et al., Substance P, Ed. by US Yon Euler and B. Pernow, Raven Press, New York (1977), pages 83 to 88, incorporated herein by reference, the products studied display an antagonism of the contractions of guinea pig ileum induced by substance P or contractions of guinea pig ileum induced by septide, at concentrations from 0.2 to 1000 nM.

Substance P is known to be involved in a certain number of pathological areas:

Agonists and antagonists of substance P, A. S. Dutta Drugs of the future, 12 (8), 782 (1987);

Substance P and pain: an updating, J. L. Henry, TINS, 3(4), 97 (1980);

Substance P in inflammatory reactions and pain, S. Rosell, Actual. Chim. Ther., 12th series, 249 (1985);

Effects of Neuropeptides on Production of Inflammatory Cytokines by Human Monocytes, M. Lotz et al., Science, 241, 1218 (1988);

Neuropeptides and the pathogenesis of allergy, Allergy, 42, 1 to 11 (1987);

Substance P in Human Essential Hypertension, J. Cardiovascular Pharmacology, 10, (suppl. 12), 5172 (1987), all incorporated herein by reference.

The study of certain isoindole derivatives of general formula (I) in the technique of A. Saria et al., Arch. Pharmacol., 324, 212–218 (1983), incorporated, herein by reference adapted to the guinea pig, has made it possible to demonstrate an inhibitory effect on the increase in capillary permeability brought about by septide (a substance P agonist), which bears evidence of an antiinflammatory activity:

| Product studied | ED$_{50}$ mg/kg p.o. |
| --- | --- |
| Example 1 | 0.004 |
| Example 2 | 1 |
| Example 4 | 0.004 |
| Example 5 | 0.32 |
| Example 7 | 0.36 |
| Example 10 | 0.05 |
| Example 13 | 0.02 |
| Example 14 | 0.2–0.4 |
| Example 18 | 1 |

Moreover, certain products according to the invention were studied in the formaldehyde pain test in guinea pigs. The ED$_{50}$ of the product is determined in this way.

| Product studied | ED$_{50}$ mg/kg p.o. |
| --- | --- |
| Example 1 | 1 |
| Example 5 | 3–30 |
| Example 9 | 3–30 |

Finally, the isoindole derivatives according to the present invention display no toxicity; they prove to be nontoxic in mice at a subcutaneous dose of 40 mg/kg.

The present invention also relates to the synergistic combination comprising at least one NK1 receptor antagonist of general formula (I) and at least one NK2 receptor antagonist.

The effects of neurokinin A are mediated principally by the NK2 receptors. Neurokinin A is involved in numerous pathologies, such as the transmission of pain, arthritis, asthma, inflammatory phenomena, psychoses, vascular tension disorders, vesical disorders, cystites, etc.

NK2 receptor antagonists (antagonists of the effects of neurokinin A) are known and are described in particular, but without limitation, in the Patent Applications EP 428 434, EP 474 561, EP 512 901, EP 515 240, FR 2 678 267, WO 92/19254 or WO 93/14084.

Without limitation, NK2 receptor antagonists can in particular be derivatives of the class of the arylalkylamines, the class of the α-substituted polypeptides or the class of the piperidine derivatives, etc.

Possible examples of NK2 receptor antagonists from the class of the arylalkylamines are products of structure:

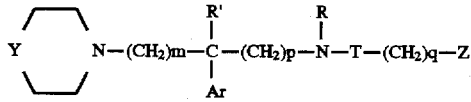

and, among these products, a specific NK2 receptor antagonist is described more particularly by X. Emonds-Alt et al., Life Science, 50, PL 100 to PL 106 (1992).

Possible examples of NK2 receptor antagonists from the class of the α-substituted polypeptides are products of structure:

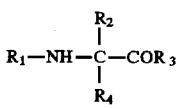

in which the radicals can be amino-acid residues.

Possible examples of NK2 receptor antagonists from the class of the piperidine derivatives are products of structure:

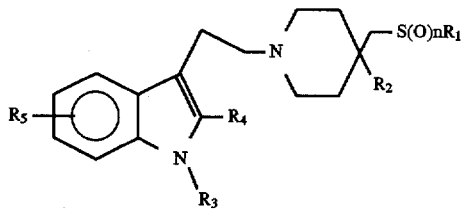

and, among these products, more specifically 1-[2-(5-fluoro-1H-indol-3-yl)ethyl]-4-[(phenylsulphinyl)methyl]-4-piperidinol.

The examples which follow, which are given without any limitation being implied, illustrate the present invention.

In the examples which follow it is understood that, unless mentioned otherwise, the proton spectra were recorded at 250 MHz in dimethyl sulphoxide; the chemical shifts are expressed in ppm.

EXAMPLE 1

(3aS,4S,6S,7aR)-6-Cyanomethyl-4-(2-methoxyphenyl)-2-[(S)-2-(2-methoxylphenyl) propionyl]perhydroisoindol-4-ol 1.0 g of potassium cyanide is added to a solution of 5.6 g of (3aS,4S,6R,7aR)-4-(2-methoxyphenyl)-2-[(S)-2-(2-methoxyphenyl)propionyl]-6-tosyloxymethylperhydroisoindol-4-ol in 50 cm³ of dimethyl sulphoxide. After stirring at 45° C. for hours, the reaction mixture is cooled to 20° C., diluted with 300 cm³ of water and then extracted twice with 50 cm³ of ethyl acetate. The organic phase is subsequently washed with 150 cm³ of water, dried. over magnesium sulphate and concentrated to dryness under reduced pressure (2.7 kPa). The residue is chromatographed on a silica gel column (particle size 0.06–0.20 mm, diameter 4.4 cm, height 50 cm), eluting under a pressure of 0.2 bar of nitrogen with a mixture of cyclohexane and ethyl acetate (40:60 by volume) and collecting fractions of 120 cm³. Evaporation to dryness of fractions 11 to 20 under reduced pressure (2.7 kPa) gives 2.9 g of (3aS,4S,6S,7aR)-6-cyanomethyl-4-(2-methoxyphenyl)-2-[(S)-2-(2-methoxyphenyl)propionyl]perhydroisoindol-4-ol in the form of a thick white foam.

$^1$H NMR spectrum (400 MHz, (CD$_3$)$_2$SO d6, δ in ppm): (at room temperature, the rotamer mixture is observed). 1.14 and 1.22 (2 d, J=7 Hz, 3H in all: CH$_3$); 1.42 and 1.70 to 1.90 (2 m, 1H each: CH$_2$ 7); 1.45 to 1.70 and 2.20 to 2.50 (2 m, 1H each: CH$_2$ 5); 2.20 to 2.50 (m, 4H: H 6—CH$_2$CN and H 7a); 2.58 and 2.72 (2 m, 1H in all: H 3a); 2.85 to 3.60 (m, 4H: NCH$_2$); 3.58–3.76–3.80 and 3.83 (4 s, 6H in all: OCH$_3$); 3.93 and 4.08 (2 q, J=7 Hz, 1H in all: ArCH); 4.28 and 4.89 (2 broad s, 1H in all: OH); 6.75 to 7.70 (m, 8H: aromatic H).

Infrared spectrum (KBr), characteristic bands (cm$^{-1}$): 3560, 3420, 3100+3070, 2960+, 2930, 2880, 2850, 2840, 2245, 1635, 1600+1585+1490, 1455+1440, 1240, 1105, 1060, 1030, 965, 755.

(3aS,4S,6R,7aR)-4-(2-methoxyphenyl)-2-[(S)-2-(2-methoxyphenyl)propionyl]-6-tosyloxymethyl perhydroisoindol-4-ol can be prepared as follows:

20.1 g of p-toluenesulphonyl chloride are added to a solution of 23.2 g of 6-hydroxymethyl-4-(2-methoxyphenyl)-2-[(S)-2-(2-methoxyphenyl)propionyl]perhydroisoindol-4-ol (mixture of the 2 diastereoisomers, 3aR,4R,6S,7aS,S and 3aS,4S,6R,7aR,S) and 14.9 cm³ of triethylamine in 300 cm³ of dichloromethane. After stirring at 20° C. for 48 hours, the reaction mixture is washed with 150 cm³ of water, then dried over magnesium sulphate and concentrated to dryness under reduced pressure (2.7 kPa). The residue is chromatographed on a silica gel column (particle size 0.06–0.20 mm, diameter 8.0 cm, height 45 cm), eluting under a pressure of 0.8 bar of nitrogen with a mixture of cyclohexane and ethyl acetate (50:50 by volume) and collecting fractions of 500 cm³. Fractions 14 to 17 are concentrated to dryness under reduced pressure. The residue obtained is subsequently chromatographed on a silica gel column (particle size 0.04–0.06 mm, diameter 7.5 cm, height 60 cm), eluting under a pressure of 0.8 bar of nitrogen with a mixture of cyclohexane and ethyl acetate (60:40 then 50:50 by volume) and collecting fractions of 500 cm³. Evaporation to dryness of fractions 22 to 26 gives 6.5 g of the (3aS,4S,6R,7aR)-4-(2-methoxyphenyl)-2-[(S)-2-(2-methoxyphenyl)propionyl]-6-tosyloxymethyl perhydroisoindol-4-ol diastereoisomer in the form of a thick white foam.

¹H NMR spectrum (250 MHz, (CD₃)₂SO d6, δ in ppm): (at room temperature, the rotamer mixture is observed). 1.10 to 1.30 (m, 3H: CH₃); 1.20 to 1..80 (m, 3H: CH₂ 7 and 1H of CH₂ 5); 2.10 to 2.30 (m, 1H: the other H of the CH₂ 5); 2.20 to 2.50 (m, 2H: H 6 and H 7a); 2.43 (s, 3H: ArCH₃); 2.55 and 2.68 (2 m, 1H: H 3a); 2.80 to 3.60 (m, 4H: NCH₂); 3.60–3.75–3.79 and 3.87 (4s, 6H in all: OCH₃); 3.80 to 4.00 (m, 2H: CH₂O); 4.00 to 4.15 (m, 1H: ArCH); 4.20 and 4.80 (2 broad s, 1H in all: OH); 6.60 to 7.65 (m, 8H: aromatic H); 7.50 and 7.82 (2 m, 2H each: aromatic H of the tosyl).

Infrared spectrum (KBr), characteristic bands (cm⁻¹): 3560+3510, 3425, 3110+3070, 2930, 2890, 2860, 2840, 1635, 1600+1580+1495, 1460+1430, 1360, 1240, 1190+1180, 1100, 1060, 1035, 965, 815, 760, 670, 580+560.

6-Hydroxymethyl-4-(2-methoxyphenyl )-2-[(S)-2-(2-methoxyphenyl)propionyl]perhydroisoindol-4-ol (mixture of the 2 diastereoisomers, 3aR,4R,6S,7aS,S and 3aS,4S,6R,7aR, S) can be prepared as follows:

2.1 g of 1-(3-dimethylaminopropyl)-3-ethylcarbodiimide are added to a solution of 2.77 g of (3aRS,4RS,6SR,7aSR)-6-hydroxymethyl-4-(2-methoxyphenyl)perhydroisoindol-4-ol, 1.80 g of (S)-2-(2-methoxyphenyl)propionic acid and 30 mg of hydroxybenzotriazole hydrate in 80 cm³ of dichloromethane. After stirring at 20° C. for 20 hours, the reaction mixture is washed with 40 cm³ of water, dried over magnesium sulphate and concentrated to dryness under reduced pressure (2.7 kPa). The residue is chromatographed on a silica gel column (particle size 0.06–0.20 mm, height 40 cm) in a mixture of cyclohexane and ethyl acetate (30:70 by volume) and then in a mixture of ethyl acetate and methanol (90:10 by volume). Evaporation of the eluent and drying. I under reduced pressure (2.7 kPa) give 3.6 g of 6-hydroxymethyl-4-(2-methoxyphenyl)-2-[(S)-2-(2-methoxyphenyl)propionyl]perhydroisoindol-4-ol (mixture of the 2 diastereoisomers, 3aR,4R,6S,7aS,S and 3aS,4S,6R, 7aR, S) in the form of a white solid. M.p._K=178° C.

¹H NMR spectrum (250 MHz, (CD₃)₂SO d6 with addition of several drops of CD₃COOD-d₄, at a temperature of 393 K, δ in ppm): the mixture of two diastereisomers is observed. 1.20 to 2.10 (m, 4H: CH₂ 7 and CH₂ 5); 1.29 and 1.33 (2d, J=7 Hz, 3H in all: CH₃); 2.05 to 2.30 (m, 1H: H 6); 2.40 to 2.60 (m, 1H: H 7a); 2.75 to 2.90 (m, 1H: H 3a); 2.90 to 3.60 (m, 4H: NCH₂); 3.35 (d, J=5.5 HZ, 2H: CH₂O); 3.76–3.78–3.83 and 3.85 (4s, 6H in all: OCH₃); 4.05 to 4.25 (m, 1H: ArCH); 6.85 to 7.65 (m, 8H: aromatic H).

Infrared spectrum (characteristic bands in cm⁻¹): 3480, 3425, 3110+3070, 2930, 2880, 2840, 1625, 1600+1585+1495+1490, 1460, 1410, 1240, 1110, 1080, 1060, 1030, 970, 750.

(3aRS,4RS,6SR,7aSR)-6-Hydroxymethyl-4-(2-methoxyphenyl)perhydroisoindol-4-ol can be prepared as follows:

A suspension of 3.1 g of (3aRS,4RS,6SR,7aSR)-2-benzyl-6-hydroxymethyl-4-(2-methoxyphenyl) perhydroisoindol-4-ol and 0.5 g of 20% palladium hydroxide on carbon black in 75 cm³ of ethanol is hydrogenated under atmospheric pressure at 60° C. for 3 hours. The reaction mixture is subsequently filtered and concentrated to dryness under reduced pressure (2.7 kPa). 3.0 g of (3aRS, 4RS,6SR,7aSR)-6-hydroxymethyl-4-(2-methoxyphenyl) perhydroisoindol-4-ol are obtained in the form of a thick white foam.

NMR (DMSO-d₆+AcOD, 250 MHz), δ (ppm): 1.41 and 1.90 (m and d, 2×1H, CH-C$\underline{H}_2$—CH), 1.60 and 2.22 (d and t, 2×1H, C—C$\underline{H}_2$—CH), 2.10 (m, 1H, C$\underline{H}$—CH₂OH), 2.59 (m, 1H, CH₂—C$\underline{H}$—CH), 2.95 (m, 1H, CH—C$\underline{H}$—C), 2.95 (m, 2H, N—C$\underline{H}_2$—CH), 3.20 and 3.32 (m, 2H, N—C$\underline{H}_2$—CH), 3.30 (s, 2H, O—C$\underline{H}_2$—CH), 3.81 (s, 3H, OC$\underline{H}_3$), 7.00–7.64 (m, 4H, aromatic).

Infrared spectrum (KBr), characteristic bands (cm⁻¹): 3420, 3075, 2920, 2880, 1595, 1575, 1485, 1460, 1235, 1055, 1030, 755.

(3aRS,4RS,6SR,7aSR)-2-Benzyl-6-hydroxymethyl-4-(2-methoxyphenyl)perhydroisoindol-4-ol can be prepared as follows:

A solution of 8.0 g of (3aRS,6SR,7aSR)-6-acetoxymethyl-2-benzylperhydroisoindol-4-one in 60 cm³ of anhydrous tetrahydrofuran is added to a suspension of 2-methoxyphenylmagnesium bromide (prepared from 24.9 cm³ of 2-bromoanisole and 4.86 g of magnesium) in 200 cm³ of anhydrous tetrahydrofuran. The reaction mixture is stirred at 20° C. for 20 hours, then cooled to +5° C. and treated with 120 cm³ of saturated aqueous ammonium chloride solution and 100 cm³ of ethyl acetate. After filtration of the mixture, the organic phase is washed with brine, then dried over magnesium sulphate and concentrated to dryness under reduced pressure (2.7 kPa). The residue is chromatographed on a silica gel column (particle size 0.06–0.20 mm, height 40 cm) in a mixture of 1,2-dichloroethane and methanol (95:5 by volume). Recrystallization from ethyl ether gives 3.2 g of (3aRS,4RS,6SR, 7aSR)-2-benzyl-6-hydroxymethyl-4-(2-methoxyphenyl) perhydroisoindol-4-ol in the form of a white solid melting at 110° C.

Proton NMR spectrum (CDCl₃+AcOD, 250 MHz, T=333° K), δ (ppm): 1.40 and 1.85 (m and d, 2×1H, CH—C$\underline{H}_2$—CH), 1.75 and 2.05 (t and d, 2×1H, C—C$\underline{H}_2$—CH), 2.28 (m, 1H, CH₂—C$\underline{H}$—CH₂), 2.82 (m, 1H, CH₂—C$\underline{H}$—CH), 3.03 (t, 1H, CH—C$\underline{H}$—C), 3.11 and 3.50 (d, 2×1H, N—C$\underline{H}_2$—CH), 3.38 and 3.52 (t, 2×1H, N—C$\underline{H}_2$—CH), 3.50 (m, 2H, O—C$\underline{H}_2$—CH), 3.86 (s, 3H, OC$\underline{H}_3$), 4.28 and 4.40 (d, 2×1H, N—C$\underline{H}_2$Ph), 6.85–7.45 (m, 9H, aromatic).

Infrared spectrum (KBr), characteristic bands (cm⁻¹): 3560, 3420, 3060, 3025, 3005, 2910, 2850, 2800, 1590, 1575, 1495, 1480, 1230, 1055, 1030, 755, 735, 700.

(3aRS,6SR,7aSR)-6-Acetoxymethyl-2-benzylperhydroisoindol-4-one can be prepared as follows:

Two drops of trifluoroacetic acid are added to a solution of 6.5 g of 5-acetoxymethylcyclohex-2-en-1-one and 14 g of N-butoxymethyl-N-trimethylsilylmethylbenzylamine [prepared according to the method described by Y. Tarao et al., Chem. Pharm. Bull., 33., 2762 (1985)] in 60 cm³ of dry dichloromethane. On reaching reflux, the reaction mixture is maintained at the same temperature for 30 minutes and then left at 20° C. for one hour. After addition of 1.0 g of potassium carbonate, the suspension obtained is filtered, and the filtrate is concentrated to dryness under reduced pressure (2.7 kPa). The oily residue obtained is chromatographed on a silica gel column (particle size 0.06–0.2 mm, height 42 cm) in a mixture of cyclohexane and ethyl acetate (40:60 by volume) and then in ethyl acetate. 8.2 g of (3aRS,6SR,7aSR)-6-acetoxymethyl-2-benzylperhydroisoindol-4-one are obtained in the form of a yellowish oil.

Proton NMR spectrum (CDCl$_3$+AcOD, 250 MHz), δ (ppm): 1.82 (m, 2H, CH—C$\underline{H}_2$—CH), 2.03 (s, 3H, C$\underline{H}_3$CO), 2.2 (m, 1H, C$\underline{H}$), 2.27 and 2.42 (t and dd: 2×1H, —COC$\underline{H}_2$—), 2.40 and 3.60 (t, 2×21H, N—C$\underline{H}_2$—CH), 3.10 (td, 1H, C$\underline{H}$), 3.22 (m, 1H, C$\underline{H}$), 3.60 and 3.75 (m, 2×1H, N—C$\underline{H}_2$—CH), 4.00 (m, 2H, O—C$\underline{H}_2$—), 4.10 and 4.23 (d, 2×1H, N—C$\underline{H}_2$—Ph), 7.30–7.45 (m, 5H, aromatic).

Infrared spectrum (CCl$_4$), characteristic bands (cm$^{-1}$): 3105, 3090, 3065, 3030, 2920, 2795, 1745, 1712, 1605, 1585, 1495, 1455, 1425, 1365, 1240, 1035, 700.

5-Acetoxymethylcyclohex-2-en-1-one can be prepared according to the method described by Dipakranjan Mal et al., J. Chem. Soc. Perkin Trans.1, 309, (1994), incorporated herein by reference.

(S)-2-(2-Methoxyphenyl)propionic acid can be prepared, by analogy with the methods described by D. A. Evans et al., Tetrahedron, 44, 5525 (1988), incorporated herein by reference, by the following procedure:

1.52 g of lithium hydroxide are added to a solution, cooled to +5° C., of 4.1 g of (4S,5S)-4-methyl-5-phenyl-3-[(S)-2-(2-methoxyphenyl)propionyl]oxazolidin-2-one in 60 cm$^3$ of tetrahydrofuran and 30 cm$^3$ of water. The reaction mixture is stirred at this temperature for 3 hours and then, after returning to room temperature, ethyl acetate is added, the phases are separated by decanting, the aqueous phase is acidified with 1N aqueous hydrochloric acid solution and extracted with ethyl acetate, and the organic phase is dried over magnesium sulphate and concentrated to dryness under reduced pressure (2.7 kPa). The solid obtained is recrystallized from hexane, drained and dried. 0.4 g of (S)-2-(2-methoxyphenyl)propionic acid is obtained in the form of white crystals melting at 102° C. [α]$_D^{20}$=+84.6° (C=1; CHCl$_3$)

(4S,5S)-4-Methyl-5-phenyl-3-[(S)-2-(2-methoxyphenyl) propionyl]oxazolidin-2-one can be obtained as follows:

19.1 g of sodium 1,1,1,3,3,3-hexamethyldisilazanate are added to a solution, cooled to −50° C., of 10 g of (4S,5S)-4-methyl-5-phenyl-3-[(2-methoxyphenyl)acetyl]oxazolidin-2-one in 150 cm$^3$ of tetrahydrofuran, the mixture is stirred at this temperature for 45 minutes, and then 7.72 cm$^3$ of methyl iodide are added. The reaction mixture is subsequently stirred at room temperature for 15 hours, then diluted with ethyl acetate, washed with 50 cm$^3$ of water followed by 50 cm$^3$ of saturated aqueous sodium chloride solution, dried over magnesium sulphate and concentrated to dryness under reduced pressure (2.7 kPa). The residue obtained is recrystallized from isopropyl ether, drained and dried. 4.2 g of (4S,5S)-4-methyl-5-phenyl-3-[(S)-2-(2-methoxyphenyl)propionyl]oxazolidin-2-one are obtained in the form of a white solid.

(4 S,5S )-4-Methyl-5-phenyl-3-(2-methoxyphenylacetyl) oxazolidin-2-one can be obtained as follows:

9.38 g of 2-methoryphenylacetic acid are added at room temperature to a suspension of 1.89 [lacuna] of sodium hydride (80% dispersion in petroleum jelly) in 200 cm$^3$ of dry tetrahydrofuran. This suspension is cooled to −30° C., 7.77 cm$^3$ of pivaloyl chloride are added, and then finally a solution, cooled to −78° C., is added which is obtained by adding a solution of 35.27 cm$^3$ of 1.6M butyllithium in hexane to a solution, cooled to −78° C., of 10 g of (4S,5S)-4-methyl-5-phenyl-oxazolidin-2-one in 200 cm$^3$ of dry tetrahydrofuran. The reaction mixture is stirred at −30° C. for 45 minutes and then, after returning to room temperature, 200 cm$^3$ of saturated aqueous ammonium chloride solution are added followed by 500 cm$^3$ of ethyl acetate; after separation of the phases by decanting, the organic phase is washed twice with 100 cm$^3$ of water and then twice with 100 cm$^3$ of saturated aqueous sodium chloride solution, dried over magnesium sulphate and concentrated to dryness under reduced pressure (2.7 kPa). The residue is chromatographed on a silica gel column (particle size 0.04–0.06 mm, diameter 4.8 cm, height 36 cm), eluting under a pressure of 0.6 bar of nitrogen with a mixture of cyclohexane and ethyl acetate (85:15 then 80:20 by volume) and collecting fractions of 50 cm$^3$. Fractions 14 to 31 are combined and concentrated to dryness under reduced pressure (2.7 kPa). 13.6 g of (4S,5S)-4-methyl-5-phenyl-3-(2-methoxyphenylacetyl)oxazolidin-2-one are obtained in the form of a yellow oil.

EXAMPLE 2

(3aRS,4RS,6RS,7aSR)-6-Cyanomethyl-4-(2-methoxyphenyl)-2-{[2-(1-pyrrolidinyl)phenyl]acetyl} perhydroisoindol-4-ol A solution of 0.54 g of [2-(1-pyrrolidinyl)phenyl]acetic acid and 0.33 cm$^3$ of triethylamine in 20 cm$^3$ of dichloromethane, and then 8.6 mg of hydroxybenzotriazole hydrate and 0.47 g of 1-(3-dimethylaminopropyl)-3-ethylcarbodiimide are added to a solution of 0.64 g of (3aRS,4RS,6RS,7aSR)-6-cyanomethyl-4-(2-methoxyphenyl)perhydroisoindol-4-ol trifluoroacetate and 0.33 cm$^3$ of triethylamine in 10 cm$^3$ of dichloromethane. After stirring at 20° C. for 20 hours, the reaction mixture is washed with water, dried over magnesium sulphate and concentrated to dryness under reduced pressure (2.7 kPa). The residue is chromatographed on a column of alumina (particle size 50–150 μm, diameter 2 cm, height 47 cm) under a pressure of 0.3 bar of nitrogen with a mixture of cyclohexane and ethyl acetate (20:80 then 50:50 by volume) and then with ethyl acetate, collecting fractions of 25 cm$^3$. Evaporation to dryness of fractions 20 to 73 under reduced pressure (2.7 kPa) gives 240 mg of a thick foam which is triturated in acetonitrile. Filtration and drying of the solid obtained give 150 mg of (3aRS,4RS,6RS,7aSR)-6-cyanomethyl-4-(2-methoxy-phenyl)-2-{[2-(1-pyrrolidinyl)phenyl]acetyl} perhydroisoindol-4-ol are obtained in the form of a white solid. M.p.$_K$=201° C.

$^1$H NMR spectrum (400 MHz, (CD$_3$)$_2$SO d6 with addition of a few drops of CD$_3$COOD-d$_4$, δ in ppm): 1.46 and 1.92 (d (J=14 and 6 Hz) and m respectively, each 1H: CH$_2$ 7); 1.78 and 2.26 (broad d and broad t respectively, J=13 Hz, each 1H: CH$_2$ 5); 1.89 (m, 4H: CH$_2$ of pyrrolidine); 2.35 to 2.55 (m, 3H: H 6 and CH$_2$CN); 2.62 (m, 1H: H 7a); 2.84 (m, 1H: H 3a); 3.04 (m, 4H: NCH$_2$ of pyrrolidine); 2.90 to 3.65 (m, 6H: NCH$_2$ and CH$_2$Ar); 3.84 (s, 3H: OCH$_3$); 6.85 to 7.60 (m, 8H: aromatic H).

Infrared spectrum (KBr), characteristic bands (cm$^{-1}$): 3430, 3110+3070+3025, 2950, 2880+2890, 2855, 2840, 2825, 2250, 1625, 1600+1585+1495+1485, 1450, 1250, 1105, 1060, 1090, 1025, 960, 755, 587.

(3aRS,4RS,6RS,7aSR)-6-Cyanomethyl-4-(2-methoxyphenyl)perhydroisoindol-4-ol can be prepared as follows:

250 cm³ of a 6N solution of dioxane in hydrochloric acid are added slowly, while maintaining the medium at 20° C., to a solution of 142 g of (3aRS,4RS,6RS,7aSR)-6-cyanomethyl-4-(2-methoxyphenyl)-2-tert-butyloxycarbonylperhydroisoindol-4-ol in 750 cm³ of dioxane. The reaction mixture is stirred for 1 hour, concentrated to reduced volume (crystallization) and then diluted with 300 cm³ of ethyl ether. The suspension is filtered, the crystals are washed with ethyl ether and then filtered with suction and dried under reduced pressure (2.7 kPa). The (3aRS,4RS,6RS,7aSR)-6-cyano-methyl-4-(2-methoxyphenyl)perhydroisoindol-4-ol hydrochloride obtained is taken up in 400 cm³ of dichloromethane and, after addition of 160 cm³ of 4N sodium hydroxide solution, the organic phase is washed with 300 cm³ of water, dried over magnesium sulphate and then concentrated to dryness under reduced pressure (2.7 kPa). 103 g of ((3aRS,4RS,6RS,7aSR)-6-cyanomethyl-4-(2-methoxyphenyl) perhydroisoindol-4-ol are obtained in the form of a yellowish white solid.

¹H NMR spectrum (250 MHz, (CD₃)₂SO d6 with addition of a few drops of CD₃COOD-d₄, δ in ppm): 1.51 and 1.91 (d and broad d respectively, J=14 and 5.5 Hz and J=14 Hz, each 1H: CH₂ 7); 1.70 and 2.25 to 2.45 (broad d (J=12 Hz) and m, respectively, each 1H: CH₂ 5); 2.20 to 2.45 (m, 1H: H 6); 2.48 (m, 2H: CH₂CN); 2.63 (m, 1H: H 7a); 2.85 to 3.40 (m, 5H: NCH₂ and H 3a); 3.80 (s, 3H: OCH₃); 6.95 to 7.65 (m, 4H: aromatic H).

Infrared spectrum (KBr), characteristic bands (cm⁻¹): 3345, 2980, 2950, 2950, 2785+2760+2470+2410, 2240, 1600, 1575, 1485, 1460, 1435, 1240, 1100,, 1060, 1025, 950, 765.

(3aRS,4RS,6RS,7aSR)-6-Cyanomethyl-4-(2-methoxyphenyl)perhydroisoindol-4-ol trifluoroacetate can be prepared by treating a solution of 8.5 g of (3aRS,4RS,6RS,7aSR)-6-cyanomethyl-4-(2-methoxyphenyl)-2-tert-butyloxycarbonylperhydroisoindol-4-ol in 170 cm³ of dichloromethane with 12.6 cm³ of trifluoroacetic acid at 20° C. for 4 hours. Evaporation of the reaction solution to dryness under reduced pressure (2.7 kPa) gives 8.8 g of (3aRS,4RS,6RS,7aSR)-6-cyanomethyl-4-(2-methoxyphenyl)perhydroisoindol-4-ol trifluoroacetate in the form of an oil which will be used as it is for the rest of the synthesis.

(3aRS,4RS,6RS,7aSR)-6-Cyanomethyl-4-(2-methoxyphenyl)-2-tert-butyloxycarbonyl perhydroisoindol-4-ol can be prepared as follows:

40 g of potassium cyanide are added carefully to a solution of 215 g of (3aRS,4RS,6SR,7aSR)-4-(2-methoxyphenyl)-2-tert-butyloxycarbonyl-6-tosyloxymethylperhydroisoindol-4-ol in 800 cm³ of dimethyl sulphoxide. The reaction mixture is stirred at 50° C. for 20 hours, diluted with 1 liter of water and extracted with twice 200 cm³ and then 100 cm³ of ethyl acetate. The combined organic extracts are washed with twice 500 cm³ of water, dried over magnesium sulphate and then concentrated to dryness under reduced pressure (2.7 kPa). The residue obtained is recrystallized from 200 cm³ of ethyl ether, and the crystals are washed with the same solvent, drained and then dried under reduced pressure (2.7 kPa). 142 g of (3aRS,4RS,6RS,7aSR)-6-cyanomethyl-4-(2-methoxyphenyl)-2-tert-butyloxycarbonylperhydroisoindol-4-ol are obtained in the form of a white solid. M.p.$_K$=149° C.

(3aRS,4RS,6SR,7aSR)-4-(2-Methoxyphenyl)-2-tert-butyloxycarbonyl-6-tosyloxymethylperhydroisoindol-4-ol can be prepared as follows:

A solution of 12.07 g .of (3aRS,6SR,7aSR)-2-tert-butyloxycarbonyl-6-tosyloxymethylperhydroisoindol-4-one in 50 cm³ of anhydrous tetrahydrofuran is run over a period of 15 minutes into a suspension, cooled to +5° C., of 2-methoxyphenylmagnesiumbromide (prepared from 6.4 cm³ of 2-bromoanisole and 1.24 g of magnesium) in 200 cm³ of anhydrous tetrahydrofuran. The reaction mixture is stirred at 20° C. for one hour, cooled to +5° C., treated with 250 cm³ of saturated aqueous ammonium chloride solution and extracted with 200 cm³ of ethyl acetate. The organic phase is washed with 300 cm³ of water, dried over magnesium sulphate and concentrated to dryness under reduced pressure (2.7 kPa). The oily residue is recrystallized from a mixture of ethyl acetate and diisopropyl ether, and the crystals are filtered, washed with diisopropyl ether, subjected to suction and then dried under reduced pressure (2.7 kPa). 11.38 g of (3aRS,4RS,6SR,7aSR)-4-(2-methoxyphenyl)-2-tert-butyloxycarbonyl-6-tosyloxymethylperhydroisoindol-4-ol are obtained in the form of white crystals. M.p.$_K$=153° C.

(3aRS,6SR,7aSR)-2-tert-Butyloxycarbonyl-6-tosyloxymethylperhydroisoindol-4-one can be prepared as follows:

17.5 g of p-toluenesulphonyl chloride are added to a solution of 12.4 g of (3aRS,6SR,7aSR)-6-hydroxymethyl-2-tert-butyloxycarbonylperhydroisoindol-4-one and 12.9 cm³ of triethylamine in 250 cm³ of dichloromethane. The mixture is stirred at room temperature for 20 hours, washed with 200 cm³ of water, dried over magnesium sulphate and then concentrated to dryness under reduced pressure (2.7 kPa). The residue obtained is chromatographed on a silica gel column (diameter 7 cm, particle size 0.06–0.20 mm, height 70 cm), eluting under a pressure of 0.7 bar of nitrogen with a mixture of cyclohexane and ethyl acetate (60:40 by volume) and collecting fractions of 250 cm³. Evaporation to dryness of fractions 16 to 24 under reduced pressure (2.7 kPa) gives 12.6 g of (3aRS,6SR, 7aSR)-2- tert-butyloxycarbonyl-6-tosyloxymethylperhydroisoindol-4-one in the form of an oil.

¹H NMR spectrum (200 MHz, CDCl₃, δ in ppm): 1.42 (s, 9H: C(CH₃)₃); 1.70 to 2.50 (m, 5H: CH₂ 7—H 6 and CH₂ 5); 2.45 (s, 3H: ArCH₃); 2.70 to 3.00 and 3.40 (2 m, 3H and 1H respectively: NCH₂ 1—H 3a and H 7a); 3.18 and 4.08 (2 m, each 1H: NCH₂ 3); 3.93 (d, J=4 Hz, 2H: CH₂O); 7.36 (d, J=7.5 Hz, 2H: aromatic H ortho of CH₃); 7.78 (d, J=7.5 Hz, 2H: aromatic H meta of CH₃) .

Infrared spectrum (CCl₄) , characteristic bands (cm⁻¹): 2980, 2930, 2900, 1720, 1700, 1600+1495, 1480, 1455, 1405, 1395, 1365, 1190+1180, 1165, 1110, 1100+1020, 980, 880, 825, 670+570+555.

(3aRS,6SR,7aSR)-6-Hydroxymethyl-2-tert-butyloxycarbonylperhydroisoindol-4-one can be prepared by the hydrogenation, under atmospheric pressure over two hours, of a suspension, which has been brought to 50° C., of 513 g of (3aRS,6SR,7aSR)-6-acetoxymethyl-2-benzylperhydroisoindol-4-one and 103 g of 20% palladium hydroxide on carbon black in 5.13 liters of ethanol and 157 cm³ of 35% hydrochloric acid. The reaction mixture is subsequently filtered and concentrated to dryness under reduced pressure (2.7 kPa). An oil is obtained to which is added, with stirring, 3.45 liters of water, 174.1 g of sodium carbonate and 9.7 liters of dioxane. To the solution obtained is slowly added a solution of 386.2 g of di-tert-butyl dicarbonate in 1.5 liters of dioxane. The suspension obtained is stirred at room temperature for 72 hours and filtered, and the insoluble material is washed with twice 0.5 liters of dioxane. The combined filtrates are concentrated to reduced volume and then extracted with 3 liters and then 1.5 liters of ethyl acetate. The organic phase is washed while cold with 2.5 liters of 3% aqueous citric acid solution, two liters of water and two liters of brine and then dried over magnesium sulphate and concentrated to dryness under reduced pressure. To the red oil obtained are added 22 liters of methanol, 6.6 liters of water and 660 g of sodium carbonate. The mixture is stirred at 60° C. for 2 hours and then at 20° C. for 20 hours. After concentration to reduced volume, the mixture is extracted with 3 liters and 1.5 liters of ethyl acetate, and the extracts are washed with 4 times one liter of brine and then dried over magnesium sulphate and concentrated to dryness under reduced pressure. 353 g of (3aRS,6SR,7aSR) -6-hydroxymethyl-2-tert- butyloxycarbonylperhydroisoindol-4-one are obtained in the form of a red oil.

$^1$H NMR spectrum (250 MHz, CDCl$_3$, at a temperature of 333K, δ in ppm): 1.47 (s, 9H: C(CH$_3$)$_3$); 1.75 to 2.00 (m, 2H: CH$_2$ 7); 2.10 to 2.30 (m, 1H: H 6); 2.23 and 2.52 (t and broad d respectively, J=13 Hz, each 1H: CH$_2$ 5); 2.80 (m, 1H: H 3a); 2.80 to 3.10 and 3.45 (2 m, 2H and 1H respectively: NCH$_2$ 1 and H 7a); 3.22 and 4.08 (dd and broad d respectively, J=11.5 and 7 Hz and J=11.5 Hz, each 1H: NCH$_2$ 3); 3.60 (d, J=6 Hz, 2H: CH$_2$O).

Infrared spectrum (CCl$_4$), characteristic bands (cm$^{-1}$): 3635, 3440, 2980, 2920+2930, 2880, 1720, 1695+1680, 1480, 1455+1445, 1405, 1395+1365, 1240, 1165, 1110, 1060+1050, 875.

[2-(1-Pyrrolidinyl)phenyl]acetic acid can be prepared by the following method:

A mixture of 10.7 g of 2-(2-bromophenyl)acetic acid, 20 cm$^3$ of pyrrolidine and 1.66 g of copper acetate is heated at 90° C. with stirring for 2 hours; after return to room temperature, the reaction mixture is concentrated to dryness under reduced pressure (2.7 kPa). The residue is chromatographed on a silica gel column (0.2–0.063 mm, diameter 5 cm, height 55 cm), eluting with 1000 cm$^3$ of 1,2-dichloroethane then with mixtures of 1,2-dichloroethane and methanol (proportions by volume): 1000 cm$^3$ (98:2), 2000 cm$^3$ (97:3), 1000 cm$^3$ (96:4) and 1000 cm$^3$ (95:5) and collecting fractions of 250 cm$^3$. Fractions 21 to 29 are combined and concentrated to dryness under reduced pressure (2.7 kPa). 2 g of 2-[2-(1-pyrrolidinyl)phenyl]acetic acid are obtained in the form of an orange-coloured oil.

EXAMPLE 3

(3aRS,4RS,6RS,7aSR)-6-Cyanomethyl-2-[(2,6-dimethoxyphenyl)acetyl]-4-(2-methoxyphenyl) perhydroisoindol-4-ol can be prepared by proceeding in accordance with the method described in Example 2, from 0.5 g of (3aRS,4RS,6RS,7aSR)-6-cyanomethyl-4-(2-methoxyphenyl)perhydroisoindol-4-ol, 50 cm$^3$ of dichloromethane, 0.05 g of hydroxybenzotriazole hydrate, 0.34 g of (2,6-dimethoxyphenyl)acetic acid and 0.37 g of 1-(3-dimethylaminopropyl)-3-ethylcarbodiimide. Purification by chromatography gives 0.25 g of (3aRS,4RS,6RS, 7aSR)-6-cyanomethyl-2-[(2,6-dimethoxyphenyl)acetyl]-4-(2-methoxyphenyl)perhydroisoindol-4-ol in the form of a white solid. M.p.$_K$=198° C.

(2,6-Dimethoxyphenyl)acetic acid can be prepared according to the method of F. E. King and M. F. Grundon., Chem. Soc. Transactions, 3547–3552 (1950), both incorporated herein by reference.

EXAMPLE 4

(3aS,4S,6S,7aR)-6-Cyanomethyl-2-[(S)-2-(2-hydroxyphenyl)propionyl]-4-(2-methoxyphenyl) perhydroisoindol-4-ol 0.02 g of benzotriazol hydrate and 2.21 g of 1-(3-dimethylaminopropyl)-3-ethylcarbodiimide are added to a solution of 3 g of (3aRS,4RS,6RS,7aSR)-6-cyanomethyl-4-(2-methoxyphenyl)perhydroisoindol-4-ol trifluoroacetate, 2.69 g of (S)-2-(2-benzyloxyphenyl)propionic acid and 1.49 cm$^3$ of triethylamine in 30 cm$^3$ of dichloromethane. The reaction mixture is stirred at room temperature for 20 hours, washed with twice 50 cm$^3$ of water, dried over magnesium sulphate and concentrated to dryness under reduced pressure (2.7 kPa). The residue is chromatographed on a silica gel column (particle size 0.04–0.06 mm, diameter 4.8 cm, height 44 cm), eluting under a pressure of 0.4 bar of nitrogen with a mixture of diisopropyl ether and ethyl acetate (75:25 then 60:40 then 50:50 by volume, finishing with ethyl acetate) and collecting fractions of 125 cm$^3$. Fractions 65 to 73 are concentrated to dryness under reduced pressure (2.7 kPa). 0.8 g of the diastereoisomer is obtained: (3aS,4S,6S, 7aR)-6-cyanomethyl-2-[(S)-2-(2-benzyloxyphenyl) propionyl]-4-(2-methoxyphenyl)perhydroisoindol-4-ol in the form of a thick white foam.

$^1$H NMR spectrum (400 MHz, (CD$_3$)$_2$SO d6, δ in ppm): (at room temperature the rotamer mixture is observed). 1.15 and 1.25 (2 d, J=6.5 Hz, 3H in all: CH$_3$); 1.35 to 1.90 (m, 3H: CH$_2$ 7 and 1H of CH$_2$ 5); 2.10 to 2.40 (m, 2H: the other H of CH$_2$ 5 and H 6); 2.20 to 2.60 (m, 3H: CH$_2$CN and H 7a); 2.61 and 2.68 (2 m, 1H in all: H 3a); 2.85 to 3.55 (m, 4H: NCH$_2$); 3.78 and 3.81 (2 s, 3H in all: OCH$_3$); 3.85 and 4.12 (2 q, J=6.5 Hz, 1H in all: ArCH); 4.30 and 4.83 (2 broad s, 1H in all: OH); 4.67–4.98 and 5.14 (2d (J=11 Hz) and s respectively, 2H in all: OCH$_2$Ar); 6.60 to 7.60 (m, 13H: aromatic H).

Infrared spectrum (KBr), characteristic bands (cm$^{-1}$): 3410, 3110+3065+3030, 2930, 2880, 2835, 2245, 1630, 1600+1590+1495, 1450+1435, 1240, 1120+1110, 1060+1050, 1025, 960, 755, 700.

(3aS,4S,6S,7aR)-6-Cyanomethyl-2-[(S)-2-(2-hydroxyphenyl)propionyl]-4-(2-methoxyphenyl) perhydroisoindol-4-ol can be prepared by hydrogenation, under atmospheric pressure for 2 hours, of a suspension of 0.59 g of (3aS,4S,6S,7aR)-6-cyanomethyl-2-[(S)-2-(2-benzyloxyphenyl)propionyl]-4-(2-methoxyphenyl) perhydroisoindol-4-ol and 0.06 g of 20% palladium hydroxide on carbon black in 30 cm$^3$ of ethanol. The reaction mixture is subsequently filtered, and concentrated to dryness under reduced pressure (2.7 kPa). The residue is triturated in diisopropyl ether, the suspension is filtered and the solid obtained is dried under reduced pressure (2.7 kPa). 0.42 g of (3aS,4S,6S,7aR)-6-cyanomethyl-2-[(S)-2-(2-hydroxyphenyl) propionyl]-4-(2-methoxyphenyl) perhydroisoindol-4-ol is obtained in the form of an off-white solid. M.p.$_K$=128° C. (instantaneous); 106° C. (decomposition).

1H NMR spectrum (300 MHz, (CD$_3$)$_2$SO d6, δ in ppm): (at room temperature, the rotamer mixture is observed). 1.18 and 1.26 (2 d, J=7 Hz, 3H in all: CH$_3$); 1.40 to 1.95 (m, 3H: CH$_2$ 7 and 1H of CH$_2$ 5); 2.25 to 2.50 (m, 1H: the other H of CH$_2$ 5); 2.35 to 2.70 (m, 4H: H 6—CH$_2$CN and H 7a); 2.62 and 2.74 (2 m, 1H in all: H 3a); 2.90 to 3.75 (m, 4H: NCH$_2$); 3.76 and 3.81 (2 s, 3H in all: OCH$_3$); 3.88 and 4.06 (2 q, J=7 Hz, 1H in all: ArCH); 4.30 and 4.92 (2 broad s, 1H in all: OH); 6.75 to 7.70 (m, 8H: aromatic H); 9.50 and 9.85 (2 m, 1H in all: ArOH).

Infrared spectrum (KBr), characteristic bands (cm$^{-1}$): 3430, 3070+3010, 2970+2930, 2885+2860, 2835, 2780+2730+2635, 2250, 1620+1595, 1490, 1460, 1435, 1255+1235, 1105, 1025, 960, 755.

(S)-2-(2-Benzyloxyphenyl)propionic acid can be prepared as follows:

A solution of 1.07 g of (1R,2S)-N-[(S)-2-(2-benzyloxyphenyl) propionyl]camphor-2,10-sultam in a mixture of 0.47 cm³ of 30% aqueous sodium hydroxide solution and 10 cm³ of tetrahydrofuran is stirred at room temperature for 48 hours. The reaction mixture is concentrated to dryness under reduced pressure (2.7 kPa) and then the residue is diluted with 20 cm³ of distilled water, the aqueous phase is extracted with 25 cm³ of dichloromethane and then acidified with 3 cm³ of 37% aqueous hydrochloric acid solution and finally extracted 3 times with 25 cm³ of dichloromethane. The organic phase is dried over magnesium sulphate and concentrated to dryness under reduced pressure (2.7 kPa). 0.5 g of (S)-2-(2-benzyloxyphenyl)propionic acid is obtained in the form of a colourless oil.

Proton NMR spectrum (CDCl₃): 1.5 (d, 3H of $CH_3$—CH); 4.18 (q, 1H of CH—$CH_3$); 5.1 (2H of $OCH_2$); 6.95 to 7.45 (m, 9H aromatic).

(1R,2S)-N-[(S)-2-(2-Benzyloxyphenyl)propionyl] camphor-2,10-sultam can be prepared as follows:

1.62 g of potassium tert-butylate are added in portions to a solution of 4.1 g of (1R,2S)-N-[(2-benzyloxyphenyl) acetyl]camphor-2,10-sultam in 40 cm³ of tetrahydrofuran, cooled to −78° C., and then a solution of 2.63 cm³ of methyl iodide in 2 cm³ of tetrahydrofuran is added dropwise to this suspension. The reaction mixture is stirred at −78° C. for 18 hours, and then 40 cm³ of saturated aqueous ammonium chloride solution are added. After returning to room temperature, the reaction mixture is extracted with 80 cm³ of ethyl acetate, and the organic phase is washed twice with 25 cm³ of saturated aqueous ammonium chloride solution, dried over magnesium sulphate and concentrated to dryness under reduced pressure (2.7 kPa). The residue is chromatographed on a Merck silica gel column (particle size 0.04–0.06 mm, diameter 4 cm, height 39 cm), eluting under a pressure of 0.3 bar of nitrogen with dichloromethane and collecting fractions of 25 cm³. Fractions 21 to 53 are combined and are concentrated to dryness under reduced pressure (2.7 kPa). The residue is recrystallized from diisopropyl ether. 1.1 g of (1R,2S)-N-[(S)-2-(2-benzyloxyphenyl)propionyl]camphor-2,10-sultam are obtained in the form of white crystals melting at 131° C.

(1R,2S)-N-[(2-Benzyloxyphenyl)acetyl]camphor-2,10-sultam can be prepared as follows:

A solution of 0.74 g of sodium hydroxide in 20 cm³ of distilled water is added dropwise to a solution, cooled to +10° C., of 3.23 g of (1R,2S)camphor-2,10-sultam in 16 cm³ of dry dichloromethane, and then 0.03 cm³ of Aliquat 336® is added. A solution of 3.9 g of (2-methoxyphenyl)acetyl chloride in 5 cm³ of dichloromethane is subsequently added dropwise at +10° C. The reaction mixture is stirred at +10° C. for 1 hour, the phases are separated by decanting, the aqueous phase is extracted with 80 cm³ of dichloromethane and the organic phases are combined, washed with 80 cm³ of distilled water, dried over magnesium sulphate and concentrated to dryness under reduced pressure (2.7 kPa). The residue is recrystallized from 15 cm³ of diisopropyl ether. 4.1 g of (1R,2S)-N-[(2-benzyloxyphenyl)acetyl]camphor-2,10-sultam are obtained in the form of white crystals melting at 116° C.

EXAMPLE 5

(3aS, 4S, 6S, 7aR)-6-Cyanomethyl-4-(2-methoxyphenyl )-2-[(2-methoxyphenyl)acetyl] perhydroisoindol-4-ol 1.82 cm³ of triethylamine, 2.0 g of 2-methoxyphenylacetic acid, 25 mg of hydroxybenzotriazole hydrate and 2.54 g of 1-(3-dimethylaminopropyl)-3-ethylcarbodiimide are added to a solution of 3.96 g of (3aS,4S,6S,7aR)-6-cyanomethyl-4-(2-methoxyphenyl)-perhydroisoindol-4-ol hydrochloride in 60 cm³ of dichloromethane. The reaction mixture is stirred at room temperature for 20 hours, washed with 50 cm³ of water, dried over magnesium sulphate and concentrated to dryness under reduced pressure. The residue is chromatographed on a silica gel column (particle size 0.06–0.20 mm, diameter 3.6 cm, height 30 cm) under a pressure of 0.5 bar of nitrogen with ethyl acetate, collecting fractions of 100 cm³. Fractions 6 to 16 are concentrated to dryness under reduced pressure (2.7 kPa), the residue is recrystallized from ethyl acetate and then from ethanol, and the crystals are filtered, washed with a little ethanol and ethyl ether, drained and then dried under reduced pressure (2.7 kPa). 1.7 g of (3aS, 4S, 6S, 7aR)-6-cyanomethyl-4-(2-methoxyphenyl)-2-[(2-methoxyphenyl) acetyl]-perhydroisoindol-4-ol are obtained in the form of white crystals. M.p.$_K$=160° C.

¹H NMR spectrum (400 MHz, CDCl₃, δ in ppm): (at room temperature, the rotamer mixture is observed). 1.58 (m, 1H: 1H of $CH_2$ 7); 1.75 to 2.15 (m, 3H: the other H of $CH_2$ 7 and $CH_2$ 5); 2.32 (m, 2H: $CH_2CN$); 2.55 (m, 1H: H 6); 2.68 and 2.77 (2 m, 1H in all: H 7a); 2.81 and 2.87 (2 m, 1H in all: H 3a); 3.35 to 3.75 (m, 6H: $NCH_2$ and $CH_2Ar$); 3;69–3.85–3.88 and 3.90 (4 s, 6H in all: $OCH_3$); 6.80 to 7.35 (m, 8H: aromatic H).

Infrared spectrum (KBr), characteristic bands (cm⁻¹): 3305, 3070+3030, 2960+2940, 2910+2900+2885+2875, 2850+2840, 2240, 1630+1610, 1600+1495, 1465+1455+1440+1425, 1245+1235, 1110, 1050, 1030, 955, 750.

(3aS,4S,6S,7aR)-6-Cyanomethyl-4-(2-methoxyphenyl) perhydroisoindol-4-ol hydrochloride can be prepared as described in Example 2, from 28.7 g of (3aS,4S,6S,7aR)-6-cyanomethyl-4-(2-methoxyphenyl)-2-tert-butyloxycarbonylperhydroisoindol-4-ol, 230 cm³ of dioxane and 70 cm³ of a 6N solution of dioxane in hydrochloric acid. 24.0 g of (3aS,4S,6S,7aR)-6-cyanomethyl-4-(2-methoxyphenyl)perhydroisoindol -4-ol hydrochloride are obtained in the form of a white solid.

¹H NMR spectrum (300 MHz, (CD₃)₂SO d6, δ in ppm): 1.53 and 1.93 (d and broad d, respectively, J=14 and 5.5 Hz and J=14 Hz, each 1H: $CH_2$ 7); 1.68 and 2.25 to 2.45 (broad d (J=12 Hz) and m, respectively, each 1H: $CH_2$ 5); 2.25 to 2.70 (m, 4H: H 6—$CH_2CN$ and H 7a); 2.85 to 3.45 (m, 5H: $NCH_2$ and H 3a); 3.83 (s, 3H: $OCH_3$); 6.95 to 7.65 (m, 4H: aromatic H).

Infrared spectrum (KBr), characteristic bands (cm⁻¹): 3330, 2975, 2950, 2915+2855, 2840, 2770+2745+2460+2380, 2245, 1595, 1570, 1480, 1455+1465, 1435, 1420, 1240, 1100, 1050, 1020, 955, 775+760.

(3aS,4S,6S,7aR)-6-Cyanomethyl-4-(2-methoxyphenyl)-2-tert-butyloxycarbonylperhydroisoindol-4-ol can be prepared as described in Example 2, from 42 g of (3aS,4S,6R, 7aR)-4-(2-methoxyphenyl)-2-tert-butyloxycarbonyl-6-tosyloxymethylperhydroisoindol-4-ol, 200 cm³ of dimethyl sulphoxide and 7.7 g of potassium cyanide. Recrystallization from a mixture of ethyl ether and diisopropyl ether gives 28.7 g of (3aS,4S,6S,7aR)-6-cyanomethyl-4-(2-methoxyphenyl)-2-tert-butyloxycarbonylperhydroisoindol-4-ol in the form of a white solid. M.p.$_K$=170° C.

(3aS,4S,6R,7aR)-4-(2-Methoxyphenyl)-2-tert-butyloxycarbonyl-6-tosyloxymethylperhydroisoindol-4-ol can be prepared by proceeding as described in Example 2, from 2-methoxyphenylmagnesium bromide (prepared from 30 cm³ of 2-bromoanisole and 5.8 g of magnesium), 200 cm³ of tetrahydrofuran, 55.6 g of (3aS,6R,7aR)-2-tert-butyloxycarbonyl-6-tosyloxymethylperhydroisoindol-4-one and 300 cm³ of tetrahydrofuran. Recrystallization from a mixture of ethyl acetate and diisopropyl ether gives 42 g of (3aS,4S,6R,7aR)-4-(2-methoxyphenyl)-2-tert-butyloxycarbonyl-6-tosyloxymethylperhydroisoindol-4-ol in the form of a white solid. M.p.$_K$=174° C.

(3aS, 6R, 7aR)-2-tert-Butyloxycarbonyl-6-tosyloxymethylperhydroisoindol-4-one can be prepared by proceeding as described in Example 2, from 35 g of (3aS, 6R,7aR)-6-hydroxymethyl-2-tert-butyloxycarbonylperhydroisoindol-4-one, 350 cm³ of dichloromethane, 36.4 cm³ of triethylamine and 49.5 g of paratoluenesulphonyl chloride. Purification by chromatography gives 55.6 g of (3aS,6R,7aR)-2-tert-butyloxycarbonyl-6-tosyloxymethylperhydroisoindol-4-one in the form of a thick foam.

¹H NMR spectrum (300 MHz, CDCl₃, δ in ppm): 1.42 (s, 9H: C(CH₃)₃); 1.70 to 2.50 (m, 5H: CH₂ 7—H 6 and CH₂ 5); 2.45 (s, 3H: ArCH₃); 2.70 to 3.00 and 3.40 (2 m, 3H and 1H respectively: NCH₂ 1—H 3a and H 7a); 3.20 and 4.08 (2 m, 1H each: NCH₂ 3); 3.93 (m, 2H: CH₂O); 7.36 (d, J=7.5 Hz, 2H: aromatic H ortho of CH₃); 7.78 (d, J=7.5 Hz, 2H: aromatic H meta of CH₃).

(3aS,6R,7aR)-6-Hydroxymethyl-2-tert-butyloxycarbonylperhydroisoindol-4-one can be prepared by hydrogenating, under atmospheric pressure for 2 hours, a mixture of 34 g of (3aS,6R,7aR)-6-acetoxymethyl-2-benzylperhydroisoindol-4-one, 6 g of palladium hydroxide on carbon black, 140 cm³ of ethanol and 12 cm³ of 35% hydrochloric acid. The reaction mixture is subsequently filtered and the filtrate is concentrated to dryness under reduced pressure (2.7 kPa). To the oil obtained are added 400 cm³ of dioxane, 140 cm³ of water, 15.2 g of sodium carbonate and 27.2 g of di-tert-butyl dicarbonate. The mixture is stirred at room temperature for 20 hours and concentrated to reduced volume (removal of the majority of the dioxane), and then 200 cm³ of methanol and 10 g of potassium carbonate are added. The mixture is heated at 50° C. for one hour, concentrated almost to dryness under reduced pressure, diluted with 100 cm³ of water and then extracted with two times 100 cm³ of ethyl acetate. The organic phase is washed with 50 cm³ of water, dried over magnesium sulphate, and concentrated to dryness under reduced pressure (2.7 kPa). 29 g of (3aS,6R,7aR)-6-hydroxymethyl-2-tert-butyloxycarbonylperhydroisoindol-4-one are obtained in the form of a yellowish oil.

¹H NMR spectrum (300 MHz, CDCl₃, δ in ppm): (at room temperature, the rotamer mixture is observed). 1.46 (broad s, 9H: C(CH₃)₃); 1.65 to 2.00 (m, 2H: CH₂ 7); 2.10 to 2.30 (m, 1H: H 6); 2.35 and 2.52 (t and broad d, respectively, J=13 Hz, each 1H: CH₂ 5); 2.80 (m, 1H: H 3a); 2.85 to 3.10 and 3.45 (2 m, 2H and 1H respectively: NCH₂ 1 and H 7a); 3.22 and 4.08 (2 m, each 1H: NCH₂ 3); 3.60 (m, 2H: CH₂O).

(3aS,6R,7aR)-6-Acetoxymethyl-2-benzylperhydroisoindol-4-one can be prepared by proceeding according to the method described in Example 1, from 80 g of (R)-5-acetoxymethylcyclohex-2-en-1-one, 168 g of N-butoxymethyl-N-trimethylsilylmethylbenzylamine, 800 cm³ of dry dichloromethane and 5 drops of trifluoroacetic acid. Purification by chromatography gives 83 g of (3aS, 6R,7aR)-6-acetoxymethyl-2-benzylperhydroisoindol-4-one in the form of an oil which is used as it is in the following step.

¹H NMR spectrum (400 MHz, CDCl₃ with addition of a few drops of CD₃COOD-d₄, δ in ppm): 1.75 to 1.95 (m, 2H: CH₂ 7); 2.03 (s, 3H: COCH₃); 2.20 (m, 1H: H 6); 2.28 and 2.52 (t and broad d respectively, J=13 Hz, each 1H: CH₂ 5); 2.40 (m, 1H: 1H of NCH₂); 3.10 (m, 1H: H 3a); 3.22 (m, 1H: H 7a); 3.50 to 3.80 (m, 3H: NCH₂ and the other H of NCH₂); 3.99 (m, 2H: CH₂O); 4.10 and 4.23 (2 d, J=13 Hz, each 1H: NCH₂Ar); 7.30 to 7.45 (m, 5H: aromatic H).

(R)-5-Acetoxymetylcyclohex-2-en-1-one can be prepared as follows:

76 cm³ of triethylmmine are added to a solution, cooled to +5° C., of 62 g of (R)-5-hydroxymethylcyclohex-2-en-1-one [prepared according to the method described by Kenji Mori et al., Tetrahedron, Vol. 48, No. 24, 8075–8082 (1990) incorporated herein by reference] in 600 cm³ of dry dichloromethane, and then 38.4 cm³ of acetyl chloride are run in over the course of 30 minutes. After stirring at +5° C. for one hour and at 20° C. for one hour, 1 liter of water is added slowly to the mixture. The separated organic phase is washed with 1 liter of water, dried over magnesium sulphate and concentrated to dryness under reduced pressure (2.7 kPa). 80 g of (R)-5-acetoxymetylcyclohex-2-en-1-one are obtained in the form of an orange-coloured oil.

¹H NMR spectrum (250 MHz, CDCl₃, δ in ppm): 2.08 (s, 3H: COCH₃); 2.10 to 2.30 (m, 1H: CH); 2.20 and 2.65 (m, 4H: CH₂); 4.05 (AB limit, 2H: CH₂O); 6.06 (d m, J=12 Hz, 1H: =CHCO); 6.98 (d m, J=12 Hz, 1H: =CH).

EXAMPLE 6

(3aS,4S,6S,7aR)-6-Cyanomethyl-2-[(2-hydroxyphenyl)acetyl]-4-(2-methoxyphenyl) perhydroisoindol-4-ol The procedure is as described in Example 4, starting from 1.61 g of (3aS,4S,6S,7aR)-6-cyanomethyl-4-(2-methoxyphenyl)perhydroisoindol-4-ol hydrochloride, 50 cm³ of dichloromethane, 0.70 cm³ of triethylamine, 1.21 g of (2-benzyloxyphenyl) acetic acid, 0.02 g of hydroxybenzotriazole hydrate and 1.05 g of 1-(3-dimethylaminopropyl) -3-ethylcarbodiimide. Purification by chromatography followed by recrystallization from ethyl acetate give 1.4 g of (3aS,4S,6S,7aR)-6-cyanomethyl-2-[(2-benzyloxyphenyl) acetyl]-4-(2-methoxyphenyl)perhydroisoindol-4-ol are obtained in the form of white crystals.

¹H NMR spectrum (400 MHz, (CD₃)₂SO d6, δ in ppm): (at room temperature, the rotamer mixture is observed). 1.45 (m, 1H: 1H of CH₂ 7); 1.61 and 2.25 to 2.50 (2 m, each 1H: CH₂ 5); 1.76 and 1.89 (2 broad d, J=14 Hz, 1H in all: the other H of CH₂ 7); 2.30 to 2.55 (m, 4H: 6—H 7a and CH₂CN); 2.73 and 2.78 (2 m, 1H in all: H 3a); 2.90 to 3.70 (m, 6H: NCH₂ and CH₂Ar); 3.82 (s, 3H: OCH₃); 4.89 and 4.91 (2 broad s, 1H in all: OH); 5.03 and 5.11 (AB limit (J=12 Hz) and s, respectively, 2H in all: OCH₂Ar); 6.85 to 7.60 (m, 13H: aromatic H).

Infrared spectrum (KBr), characteristic bands (cm⁻¹): 3420+3315, 3110+3065+3035+3005, 2940+2930+2910, 2880+2855, 2835, 2245, 1625, 1605+1590+1490+1485, 1460, 1440, 1235, 1115+1105, 1050, 1030, 960, 755+750+745, 700+695.

(3aS,4S,6S,7aR)-6-Cyanomethyl-2-[(2-hydroxyphenyl) acetyl]-4-(2-methoxyphenyl)perhydroisoindol-4-ol is obtained by proceeding as described in Example 4, from 1.3 g of (3aS,4S,6S,7aR)-6-cyanomethyl-2-[(2-benzyloxyphenyl)acetyl]-4-(2-methoxyphenyl) perhydroisoindol-4-ol, 130 cm³ of ethanol, 0.3 g of 20% palladium hydroxide on carbon black, and hydrogen. Purification by chromatography gives 0.60 g of (3aS,4S,6S,7aR) -6-cyanomethyl-2-[(2-hydroxyphenyl)acetyl]-4-(2-methoxyphenyl)perhydroisoindol-4-ol in the form of a thick white foam.

¹H NMR spectrum (300 MHz, (CD₃)₂SO d6, δ in ppm): (at room temperature, the rotamer mixture is observed). 1.50 and 1.90 (m and broad d respectively (J=14 Hz), each 1H: CH₂ 7); 1.65 and 2.25 to 2.45 (2 m, each 1H: CH₂ 5); 2.30 to 2.60 (m, 3H: H 6 and CH₂CN); 2.50 to 2.75 (m, 1H: H 7a); 2.81 and 2.89 (2 m, 1H in all: H 3a); 2.90 to 3.70 (m, 6H: NCH₂ and CH₂Ar); 3.81 and 3.82 (2s, 3H in all: OCH₃); 4.92 and 4.94 (2 broad s, 1H in all: OH); 6.70 to 7.65 (m, 8H: aromatic H); 9.80 (unresolved multiplier, 1H: ArOH).

Infrared spectrum (KBr), characteristic; bands (cm⁻¹): 3435+3250, 3070+3010, 2930, 2890+2855, 2785+2735+2635, 2250, 1625+1595, 1490, 1460, 1435, 1255+1235, 1105, 1025, 960, 755.

EXAMPLE 7

(3aS,4S,6S,7aR)-6-Cyanomethyl-2-[(3,4-dichlorophenyl)acetyl]-4-(2-methoxyphenyl)perhydroisoindol-4-ol can be prepared by proceeding as described in Example 5, from 0.65 g of (3aS,4S,6S,7aR)-6-cyanomethyl-4-(2-methoxyphenyl)perhydroisoindol-4-ol hydrochloride, 0.28 cm³ of triethylamine, 0.41 g of 3,4-dichlorophenyl acetic acid, 5 mg of hydroxybenzotriazol hydrate and 0.42 g of 1-(3-dimethylaminopropyl)-3-ethylcarbodiimide. Purification by chromatography followed by recrystallization from ethyl acetate give 0.35 g of (3aS,4S,6S,7aR)-6-cyanomethyl-2-[(3,4-dichlorophenyl)acetyl]-4-(2-methoxyphenyl)perhydroisoindol-4-ol in the form of white crystals. M.p.$_K$=170° C.

¹H NMR spectrum (400 MHz, (CD₃)₂SO d6, δ in ppm): (at room temperature, the rotamer mixture is observed). 1.48 and 1.89 (m and broad d, respectively (J=14 Hz), each 1H: CH₂ 7); 1.63 and 2.30 to 2.45 (2 m, each 1H: CH₂ 5); 2.30 to 2.55 (m, 3H: H 6 and CH₂CN); 2.55 and 2.63 (2 m, 1H in all: H 7a); 2.79 and 2.85 (2 m, 1H in all: H 3a); 2.90 to 3.70 (m, 6H: NCH₂—CH₂Ar); 3.80 and 3.82 (2 s, 3H in all: OCH₃); 4.88 and 4.92 (2 broad s, 1H in all: OH); 6.90 to 7.60 (m, 7H: aromatic H).

Infrared spectrum (KBr), characteristic; bands (cm⁻¹): 3410, 3070, 2930, 2885+2850, 2835, 2245, 1630, 1600+1580+1560+1485+1470, 1460+1435, 1235, 1130, 1105, 1030, 960, 875+810, 755.

EXAMPLE 8

(3aS,4S,6S,7aR)-6-Cyanomethyl-2-[(3-indolyl)acetyl]-4-(2-methoxyphenyl) perhydroisoindol-4-ol can be prepared by proceeding as described in Example 5, from 0.65 g of (3aS,4S,6S,7aR)-6-cyanomethyl-4-(2-methoxyphenyl) perhydroisoindol-4-ol hydrochloride, 0.35 g of 3-indolylacetic acid, 0.05 g of hydroxybenzotriazole hydrate, 0.28 cm³ of triethylamine and 0.42 g of 1-(3-dimethylaminopropyl)-3-ethylcarbodiimide. Purification by chromatography and recrystallization from ethyl acetate give 0.32 g of (3aS,4S,6S,7aR)-6-cyanomethyl-2-[(3-indolyl) acetyl]-4-(2-methoxyphenyl) perhydroisoindol-4-ol in the form of white crystals. M.p.$_K$=220° C.

¹H NMR spectrum (400 MHz, (CD₃)₂SO d6, δ in ppm): (at room temperature the rotamer mixture is observed). 1.48 and 1.88 (m and broad d, respectively (J=14 Hz), each 1H: CH₂ 7); 1.63 and 2.25 to 2.55 (2 m, each 1H: CH₂ 5); 2.25 to 2.55 (m, 3H: H 6 and CH₂CN); 2.50 to 2.70 (m, 1H: H 7a); 2.77 and 2.86 (2 m, 1H in all: H 3a); 2.90 to 3.80 (m, 6H: NCH₂ and CH₂Ar); 3.78 and 3.80 (2 s, 3H in all: OCH₃); 4.90 and 4.93 (2 broad s, 1H in all: OH); 6.90 to 7.65 (m, 9H: aromatic H); 10.84 and 10.88 (2 broad s, 1H in all: NH).

Infrared spectrum (KBr), characteristic bands (cm⁻¹): 3535, 3430, 3230, 3105+3080+3055+3025, 2960, 2925+2905, 2880, 2855, 2840, 2250, 1630, 1583+14190, 1460, 1432, 1340, 1285, 1240+1235, 1115+1105, 1025, 955, 750+745.

EXAMPLE 9

(3aS,4S,6S,7aR)-2-[(S)-2-Amino-2-phenylacetyl]-6-cyanomethyl-4-(2-methoxyphenyl)perhydroisoindol-4-ol:

(3aS,4S,6S,7aR)-2-[(S)-2-tert-Butyloxycarbonylamino-2-phenylacetyl]-6-cyanomethyl-4-(2-methoxyphenyl) perhydroisoindol-4-ol is prepared as described in Example 5, from 3.22 g of (3aS,4S,6S,7aR)-6-cyanomethyl-4-(2-methoxyphenyl)perhydroisoindol-4-ol hydrochloride, 1.75 cm³ of diisopropylethylamine, 2.13 g of N-tert-butyloxycarbonyl-L-phenylglycine, 50 mg of hydroxybenzotriazole hydrate and 2.1 g of 1-(3-dimethyl-aminopropyl)-3-ethylcarbodiimide. The crude product is chroma(particle si a silica gel column (particle size 0.06–0.20 mm, diameter 4 cm, height 30 cm) under a pressure of 0.5 bar of nitrogen in a mixture of ethyl acetate and cyclohexane (50:50 by volume), collecting fractions of 120 cm³. Fractions 4 to 16 are concentrated to dryness under reduced pressure (2.7 kPa). 4.55 g of (3aS,4S,6S,7aR)-2-[(S)-2-tert-butyloxycarbonylamino-2-phenylacetyl]-6-cyanomethyl-4-(2-methoxyphenyl)-perhydroisoindol-4-ol are obtained in the form of a thick off-white foam.

¹H NMR spectrum (300 MHz, (CD₃)₂SO d6, δ in ppm): (at room temperature, the rotamer mixture is observed). 1.39 and 1.43 (2 s, 9H in all: C(CH₃)₃; 1.40 to 2.00 (m, 3H: CH₂ 7 and 1H of CH₂ 5); 2.25 to 2.50 (m, 1H: the other H of CH₂ 5); 2.30 to 2.65 (m, 4H: H 6 and CH₂CN and H 7a); 2.68 and 2.75 (2 m, 1H in all: H 3a); 2.90 to 3.80 (m, 4H: NCH₂); 3.78 and 3.81 (2 s, 3H in all: OCH₃); 4.54 and 4.98 (2 broad s, 1H in all: OH); 5.12 and 5.30 (2 d, J=10.5 Hz, 1H in all: ArCH); 6.70 to 7.70 (m, 9H: aromatic H).

Infrared spectrum (KBr), characteristic bands (cm⁻¹): 3430, 3110+3070+3035, 2980, 2935, 2890+2860, 2840, 2250, 1715, 1645, 1600+1590+1500+1490, 1460+1440, 1395+1370, 1240, 1170, 1105, 1055, 1030, 955, 760, 700.

25 cm³ of a 6N solution of dioxane in hydrochloric acid are added to a solution of 4.5 g of (3aS,4S,6S,7aR)-2-[(S)-2-tert-butyloxycarbonylamino-2-phenylacetyl]-6-cyanomethyl-4-(2-methoxyphenyl)perhydroisoindol-4-ol in 50 cm³ of dioxane. The reaction mixture is stirred at room temperature for one hour and then concentrated to dryness under reduced pressure (2.7 kPa). The residue is taken up in 50 cm³ of ethyl acetate, and 20 cm³ of 1N aqueous sodium hydroxide solution are added. After stirring, the organic phase is separated, washed with water, dried over magnesium sulphate and then concentrated to dryness under reduced pressure (2.7 kPa). The residue obtained is recrystallized from 5 cm³ of acetonitrile, and the crystals are washed with ethyl ether, drained and then dried under reduced pressure (2.7 kPa). 2.3 g of the compound (3aS,4S,6S,7aR)-2-[(S)-2-amino-2-phenyl-acetyl]-6-cyanomethyl-4-(2-methoxyphenyl)perhydro-isoindol-4-ol are obtained in the form of white crystals. M.p.$_K$=192° C.

¹H NMR spectrum (400 MHz, (CD₃)₂SO d6, δ in ppm): (at room temperature, the rotamer mixture is observed). 1.38 to 1.95 (m, 3H: CH₂ 7 and 1H of CH₂ 5); 2.02 (unresolved multiplier, 2H: NH₂); 2.25 to 2.45 (m, 1H: the other H of CH₂ 5); 2.25 to 2.55 (m, 3H: H 6 and CH₂CN); 2.40 to 2.60 (m, 1H: H 7a); 2.68 and 2.71 (2 m, 1H in all: H 3a); 2.90 to 3.85 (m, 4H: NCH₂); 3.76 and 3.80 (2 s, 3H in all: OCH₃); 4.36 and 4.49 (2 s, 1H in all: ArCH); 4.57 and 4.97 (2 d, J=1.5 Hz, 1H in all: OH); 6.70 to 7.65 (m, 9H: aromatic H).

Infrared spectrum (KBr), characteristic bands (cm$^{-1}$): 3410, 3380+3300, 3075+3055+3025+3005, 2965+2950+ 2935, 2910+2885+2860, 2835, 2245, 1640, 1600+1580+ 1485, 1545, 1460+1445, 1245, 1105, 1030, 970, 755, 700.

EXAMPLE 10

(3aS,4S,6S,7aR)-2-{[2-Amino-2-(2-methoxyphenyl] acetyl}-6-cyanomethyl-4-(2-methoxyphenyl) perhydroisoindol-4-ol, diastereoisomer form B)

1.32 g of [(RS)-2-tert-butyloxycarbonylamino-2-(2-methoxyphenyl)]acetic acid, 0.02 g of hydroxybenzotriazol hydrate and 0.9 g of 1-(3-dimethylaminopropyl)-3-ethylcarbodiimide are added to a suspension of 1.51 g of (3aS,4S,6S,7aR)-6-cyanomethyl-4-(2-methoxyphenyl) perhydroisoindol-4-ol hydrochloride and 0.82 cm$^3$ of diisopropylamine in 30 cm$^3$ of dichloromethane. The reaction mixture is stirred at 20° C. for 20 hours, then washed with twice 50 cm$^3$ of water, dried over magnesium sulphate and concentrated to dryness under reduced pressure (2.7 kPa). The residue is chromatographed on a silica gel column (particle size 0.063–0.20 mm, diameter 3.2 cm, height 38 cm), eluting under a pressure of 0.4 bar of nitrogen with a mixture of cyclohexane oxide and ethyl acetate (50:50 then 30:70 by volume), and collecting fractions of 60 cm$^3$. Fractions 9 to 31 are evaporated to dryness under reduced pressure (2.7 kPa). An aliquot (0.80 g) of the residue obtained is subsequently chromatographed (HPLC apparatus) on a a silica gel column (particle size 6 μM, diameter 4 cm, height 10 cm), eluting under a pressure of 40 bar (flow rate 50 ml per minute) with a mixture of cyclohexane and ethyl acetate (70:30 by volume) and collecting fractions of 125 cm$^3$. Concentration to dryness of fractions 13 to 17 under reduced pressure (2.7 kPa) gives 0.19 g of (3aS,4S,6S,7aR)-2-{[2-tert-butyloxycarbonylamino-2-(2-methoxyphenyl)]acetyl}-6-cyanomethyl-4-(2-methoxyphenyl)perhydroisoindol-4-ol, diastereoisomer form B, in the form of a white solid which is used as it is in the following step.

(3aS,4S,6S,7aR)-2-{[2-Amino-2-(2-methoxyphenyl)] acetyl}-6-cyanomethyl-4-(2-methoxyphenyl) perhydroisoindol-4-ol, diastereoisomer form B, is prepared as described in Example 9, from 0.190 g of (3aS,4S,6S,7aR)-2-{[2-tert-butyloxycarbonylamino-2-(2-methoxyphenyl)] acetyl}-6-cyanomethyl-4-(2-methoxyphenyl) perhydroisoindol-4-ol, diastereoisomer form B, and 3.0 cm$^3$ of a 2N solution of dioxane in hydrochloric acid. Treatment with 2.0 cm$^3$ of 1N aqueous sodium hydroxide solution gives 0.08 g of the compound (3aS,4S,6S,7aR)-2-{[2-amino-2-(2-methoxyphenyl)]-acetyl}-6-cyanomethyl-4-(2-methoxyphenyl)perhydroisoindol-4-ol, diastereoisomer form B in the form of a white solid.

$^1$H NMR spectrum (400 MHz, (CD$_3$)$_2$SO d6, δ in ppm): (at room temperature, the rotamer mixture is observed). 1.35 to 1.90 (m, 3H: CH$_2$ 7 and 1H of CH$_2$ 5); 2.20 to 2.55 (m, 4H: H 6—the other H of CH$_2$ 5 and CH$_2$CN); 2.45 to 2.75 (m, 2H: H 7a and H 3a); 2.85 to 3.65 (m, 4H: NCH$_2$); 3.58–3.76–3.81 and 3.84 (4 s, 6H in all: OCH$_3$); 4.35 and 4.95 (2 d, J=1.5 Hz, 1H in all: OH); 4.67 and 4.80 (2 s, 1H in all: ArCH); 6.65 to 7.65 (m, 8H: aromatic H).

Infrared spectrum (KBr), characteristic bands (cm$^{-1}$): 3420+3390+3320, 3110+3075, 2970+2940, 2890+2860, 2840, 2245, 1640, 1600+1585+1490, 1560, 1455+1445, 1240, 1105, 1050, 1030, 960, 755.

[(RS)-2-tert-Butyloxycabonylamino-2-(2-methoxyphenyl)]acetic acid is prepared from orthomethoxy-benzaldehyde according to the procedure described by E. N. Chauvel et al., J. Med. Chem. (1994), 37, 1339–1346, incorporated herein by reference.

EXAMPLE 11

(3aRS,4RS,6RS,7aSR)-6-Cyanomethyl-4-phenyl-2-(2-methoxyphenylacetyl)perhydroisoindol-4-ol The procedure is as described in Example 14 below, starting from 0.63 g of (3aRS,4RS,6RS,7aSR)-6-cyanomethyl-4-phenylperhydroisoindol-4-ol hydrochloride and 0.39 g of 2-methoxyphenylacetic acid, and gives 0.56 g of (3aRS,4RS,6RS,7aSR)-6-cyanomethyl-4-phenyl-2-(2-methoxyphenylacetyl)perhydroisoindol-4-ol in the form of a thick white foam.

$^1$H NMR spectrum (400 MHz, (CD$_3$)$_2$SO d6 at a temperature of 403 K, d in ppm): 1.60 and 1.97 (m and broad d respectively (J=14 Hz), each 1H: CH$_2$ 7); 1.72 and 1.87 (m and broad d respectively, (J=14 Hz), each 1H: CH$_2$ 5); 2.40 to 2.60 (m, 3H: H 6 and CH$_2$CN); 2.50 to 2.75 (m, 1H: H 7a); 3.10 to 3.30 (m, 1H: H 3a); 3.15 to 3.80 (m, 6H: NCH$_2$ and CH$_2$Ar); about 3.80 (broad s, 3H: OCH$_3$); 4.48 (s, 1H: OH); 6.85 to 7.55 (m, 9H: aromatic H).

Infrared spectrum (KBr), characteristic bands (cm$^{-1}$): 3580, 3400, 2980+2950, 2890, 2855, 2840, 2250, 1635, 1605+1580+1495, 1450, 1250, 1115, 1050, 1035, 970.

(3aRS,4RS,6RS,7aSR)-6-Cyanomethyl-4-phenylperhydroisoindol-4-ol hydrochloride can be prepared as follows:

The procedure is as described for Example 13 below, starting from 1.05 g of (3aRS,4RS,6RS,7aSR)-6-cyanomethyl-4-phenyl-2-tert-butyloxycarbonylperhydroisoindol-4-ol and 5 cm$^3$ of a 7N solution of hydrochloric acid in dioxane, and gives 0.63 g of (3aRS,4RS,6RS,7aSR)-6-cyanomethyl-4-phenylperhydroisoindol-4-ol in the form of a thick white foam.

(3aRS,4RS,6RS,7aSR)-6-Cyanomethyl-4-phenyl-2-tert-butyloxycarbonylperhydroisoindol-4-ol can be prepared as follows:

The procedure is as described for Example 13 below, starting from 1.1 g of (3aRS,4RS,6RS,7aSR)-6-p-toluenesulphonyloxymethyl-4-phenyl-2-tert-butyloxycarbonylperhydroisoindol-4-ol and 0.214 g of potassium cyanide, and gives 1.05 g of (3aRS,4RS,6RS,7aSR)-6-cyanomethyl-4-phenyl-2-tert-butyloxycarbonylperhydroisoindol-4-ol in the form of a yellow oil.

(3aRS,4RS,6SR,7aSR)-6-p-Toluenesulphonyloxymethyl-4-phenyl-2-tert-butyloxy-carbonylperhydroisoindol-4-ol can be prepared as follows:

2 g of (3aRS,6SR,7aSR)-6-p-toluenesulphonyl-oxymethyl-2-tert-butyloxycarbonylperhydroisoindol-4-one in 20 cm$^3$ of tetrahydrofuran are added at room temperature to a solution of 1.7 g of phenylmagnesium bromide in 9 cm$^3$ of ethyl ether. The reaction mixture is stirred at reflux for 4 hours, then treated with 20 cm$^3$ of saturated aqueous ammonium chloride solution, and extracted with 50 cm$^3$ of ethyl acetate. The organic phase is washed with 20 cm$^3$ of saturated sodium chloride solution, dried over magnesium sulphate and then concentrated to dryness under reduced pressure (2.7 kPa). The residue is chromatographed on a silica gel column (particle size 0.04–0.06 mm, diameter 3 cm, height 25 cm), eluting under a pressure of 0.5 bar of nitrogen with a mixture of cyclohexane and ethyl acetate (80:20 by volume) and collecting fractions of 25 cm³. Fractions 16 to 40 are combined and then concentrated to dryness under reduced pressure (2.7 kPa). 1.08 g of (3aRS, 4RS,6SR,7aSR)-6-p-toluenesulphonyloxymethyl-4-phenyl-2-(2-methoxyphenylacetyl)perhydroisoindol-4-ol are obtained in the form of a thick white foam.

EXAMPLE 12

(3aRS,4RS,6RS,7aSR)-6-Cyanomethyl-4-(2-fluorophenyl)-2-(2-methoxyphenylacetyl)perhydroisoindol-4-ol The procedure is as described for Example 13 below, starting from 1.67 g of (3aRS,4RS,6RS,7aSR)-6-p-toluenesulphonyloxymethyl-4-(2-fluorophenyl)-2-[(2-methoxyphenylacetyl)perhydroisoindol-4-ol and 0.29 g of potassium cyanide, and gives, after purification on a silica gel column (particle size 0.04–0.06 mm, diameter 2.8 cm, height 25 cm), eluting under a pressure of 0.5 bar of nitrogen with a mixture of cyclohexane and ethyl acetate (50:50 by volume), 0.86 g of (3aRS,4RS,6RS,7aSR)-6-cyanomethyl-4-(2-fluorophenyl)-2-(2-methoxyphenylacetyl)perhydroisoindol-4-ol in the form of a thick white foam.

$^1$H NMR spectrum (400 MHz, (CD$_3$)$_2$SO d6 with addition of a few drops of CD$_3$COOD-d$_4$, δ in ppm): (at room temperature, the rotamer mixture is observed). 1.52 and 1.90 (2 m, each 1H: CH$_2$ 7); 1.82 and 2.02 (2 m, each 1H: CH$_2$ 5); 2.30 to 2.60 (m, 3H: H 6 and CH$_2$CN); 2.50 to 2.75 (m, 2H; H 7a and H 3a); 3.00 to 3.80 (m, 6H: NCH$_2$ and CH$_2$Ar); 3.68 and 3.78 (2 s, 3H in all: OCH$_3$); 6.80 to 7.70 (m, 8H: aromatic H).

Infrared spectrum (characteristic bands in cm$^{-1}$): 3340, 3080+3020, 2955+2930, 2880, 2865, 2835, 2240, 1620, 1590+1580+1500+1480, 1465+1450+1435+1425, 1250, 1210, 1110, 1055, 1025, 965, 760.

(3aRS,4RS,6SR,7aSR)-6-p-Toluenesulphonyloxymethyl-4-(2-fluorophenyl)-2-(2-methoxyphenylcetyl)perhydroisoindol-4-ol can be prepared as follows:

The procedure is as described for Example 13 below, starting from 1.67 g of (3aRS,4RS,6SR,7aSR)-6-hydroxymethyl-4-(2-fluorophenyl)-2-(2-methoxyphenylacetyl)perhydroisoindol-4-ol, 1.23 g of p-toluenesulphonyl chloride and 0.9 cm³ of triethylamine, and gives, after purification on a silica gel column (particle size 0.04–0.06 mm, diameter 3.2 cm, height 30 cm), eluting under a pressure of 0.5 bar of nitrogen with a mixture of cyclohexane and ethyl acetate (60:40 by volume), 1.67 g of (3aRS,4RS,6SR,7aSR)-6-p-toluenesulphonyloxymethyl-4-(2-fluorophenyl)-2-(2-methoxyphenylacetyl)perhydroisoindol-4-ol in the form of a thick white foam.

(3aRS,4RS,6SR,7aSR)-6-Hydroxymethyl-4-(2-fluorophenyl)-2-(2-methoxyphenylacetyl)perhydroisoindol-4-ol can be prepared as follows:

0.066 g of 1-hydroxybenzotriazole and 1.15 g of 1-(3-dimethylaminopropyl)-3-ethylcarbodiimide hydrochloride are added to a solution, cooled to 0° C., of 1.48 g of (3aRS,4RS,6SR,7aSR)-6-hydroxymethyl-4-(2-fluorophenyl)perhydroisoindol-4-ol and 0.98 g of 2-methoxyphenylacetic acid in 20 cm³ of dichloromethane. The mixture is stirred at room temperature for 18 hours and then the organic phase is washed with 20 cm³ of water and subsequently with 20 cm³ of saturated aqueous sodium chloride solution, dried over magnesium sulphate and concentrated to dryness under reduced pressure (2.7 kPa). The residue is chromatographed on a silica gel column (particle size 0.04–0.06 mm, diameter 2.8 cm, height 20 cm), eluting under a pressure of 0.5 bar of nitrogen with ethyl acetate and collecting fractions of 20 cm³. Fractions 27 to 50 are combined and then concentrated to dryness under reduced pressure (2.7 kPa). 1.33 g of (3aRS,4RS,6SR,7aSR)-6-hydroxymethyl-4-(2-fluorophenyl)-2-(2-methoxyphenylacetyl)perhydroisoindol-4-ol are obtained in the form of a thick white foam.

EXAMPLE 13

(3aS,4S,6S,7aR)-6-Cyanomethyl-4-(2-fluorophenyl)-2-[(S)-2-(2-methoxyphenyl)propionyl]perhydroisoindol-4-ol 0.35 g of potassium cyanide is added at room temperature to a solution of 1.55 g of (3aS,4S,6S,7aR)-6-p-toluenesulphonyloxymethyl-4-(2-fluorophenyl)-2-[(S)-2-(2-methoxyphenyl)propionyl]perhydroisoindol-4-ol in 15 cm³ of dimethyl sulphoxide. The reaction mixture is stirred at 50° C. for 18 hours and then diluted with 100 cm³ of dichloromethane, and the organic phase is washed with twice 50 cm³ of water then with 50 cm³ of saturated aqueous sodium chloride solution, dried over magnesium sulphate and concentrated to dryness under reduced pressure (2.7 kPa). Recrystallization from diisopropyl ether gives 1.74 g of (3aS,4S,6S,7aR)-6-cyanomethyl-4-(2-fluorophenyl)-2-[(S)-2-(2-methoxyphenyl)propionyl]perhydroisoindol-4-ol in the form of white crystals melting at 182° C.

(3aS,4S,6R,7aR)-6-p-Toluenesulphonyloxymethyl-4-(2-fluorophenyl)-2-[(S)-2-(2-methoxyphenyl)propionyl]perhydroisoindol-4-ol can be obtained as follows:

4.2 g of p-toluenesulphonyl chloride and then 3.1 cm³ of triethylamine are added at room temperature to a solution of 1.17 g of (3aS,4S,6R,7aR)-6-hydroxymethyl-4-(2-fluorophenyl)-2-[(S)-2-(2-methoxyphenyl)propionyl]perhydroisoindol-4-ol in 30 cm³ of dichloromethane. The reaction mixture is stirred at this temperature for 18 hours, then washed with twice 25 cm³ of water and then with 25 cm³ of saturated aqueous sodium chloride solution, dried over magnesium sulphate and concentrated to dryness under reduced pressure (2.7 kPa). The residue is chromatographed on a silica gel column (particle size 0.04–0.06 mm, diameter 2.8 cm, height 25 cm), eluting under a pressure of 0.8 bar of nitrogen with a mixture of cyclohexane and ethyl acetate (60:40 by volume) and collecting fractions of 25 cm³. Fractions 22 to 35 are combined and then concentrated to dryness under reduced pressure (2.7 kPa). 0.95 g of (3aS, 4S,6R,7aR)-6-p-toluenesulphonyloxymethyl-4-(2-fluorophenyl)-2-[(S)-2-(2-methoxyphenyl) propionyl] perhydroisoindol-4-ol is obtained in the form of a thick white foam.

(3aS,4S,6R,7aR)-6-Hydroxymethyl-4-(2-fluorophenyl)-2-[(S)-2-(2-methoxyphenyl)propionyl]-perhydroisoindol-4-ol can be obtained as follows:

3.35 g of carbonyldiimidazole are added at 0° C. to a solution of 3.72 g of (S)-2-(2-methoxyphenyl)propionic acid in 50 cm³ of dichloromethane, and the mixture is then stirred at this temperature for 1 hour 30 minutes. Subsequently, at 0° C., a solution of (3aRS,4RS,6SR,7aSR)-6-hydroxymethyl-4-(2-fluorophenyl)perhydroisoindol-4-ol in dichloromethane is added, which is obtained by washing a solution of 4.57 g of (3aRS,4RS,6SR,7aSR)-6-hydroxymethyl-4-(2-fluorophenyl)perhydroisoindol-4-ol hydrochloride in 50 cm³ of dichloromethane with 34.4 cm³ of 1N aqueous sodium hydroxide solution. The reaction mixture is stirred at room temperature for 18 hours and then washed with 50 cm³ of water and then with 50 cm³ of saturated aqueous sodium chloride solution, dried over magnesium sulphate and concentrated to dryness under reduced pressure (2.7 kPa). The residue is chromatographed on a silica gel column (particle size 0.04–0.06 mm, diameter 4.5 cm, height 29 cm), eluting under a pressure of 0.5 bar of nitrogen with a mixture of cyclohexane and ethyl acetate (50:50 by volume) and collecting fractions of 75 cm$^3$. Fractions 81 to 99 are combined and then concentrated to dryness under reduced pressure (2.7 kPa). 0.95 g of (3aS,4S,6R,7aR)-6-hydroxymethyl-4-(2-fluorophenyl)-2-[(S)-2-(2-methoxyphenyl)propionyl]-perhydroisoindol-4-ol in the form of a thick white foam.

(3aRS,4RS,6SR,7aSR)-6-Hydroxymethyl-4-(2-fluorophenyl)perhydroisoindol-4-ol hydrochloride can be obtained as follows:

17 cm$^3$ of a 7N solution of hydrogen chloride in dioxane is added at room temperature to a solution of 3.35 g of (3aRS,4RS,6SR,7aSR)-6-hydroxymethyl-4-(2-fluorophenyl)-2-tert-butyloxycarbonylperhydroisoindol-4-ol in 35 cm$^3$ of dioxane. The reaction mixture is stirred at this temperature for 2 hours, then concentrated to dryness under reduced pressure (2.7 kPa). Trituration in diisopropyl ether gives 2.77 g of (3aRS,4RS,6SR,7aSR)-6-hydroxymethyl-4-(]2-fluorophenyl)perhydroisoindol-4-ol in the form of a thick white foam.

(3aRS,4RS,6SR,7aSR)-6-Hydroxymethyl-4-(2-fluorophenyl)-2-tert-butyloxycarbonylperhydroisoindol-4-ol can be prepared as follows:

94.4 cm$^3$ of a 1.6M solution of butyllithium in hexane are added dropwise to a solution of 16.5 cm$^3$ of 2-fluorobromobenzene in 200 cm$^3$ of tetrahydrofuran, cooled to −78° C. The reaction mixture is stirred at −78° C. for 2 hours, and then a solution of 8.1 g of (3aRS,6SR,7aSR)-6-hydroxymethyl-2-tert-butyloxycarbonylperhydroisoindol-4-one in 20 cm$^3$ of tetrahydrofuran is added. The reaction mixture is subsequently stirred at room temperature for 48 hours, then treated with 50 cm$^3$ of saturated aqueous ammonium chloride solution and subjected to extraction with 200 cm$^3$ of ethyl acetate, and the organic phase is washed with 100 cm$^3$ of saturated sodium chloride solution, dried over magnesium sulphate and concentrated to dryness under reduced pressure (2.7 kPa). The residue is chromatographed on a silica gel column (particle size 0.04–0.06 mm, diameter 6 cm, height 35 cm), eluting under a pressure of 0.5 bar of nitrogen with a mixture of cyclohexane and ethyl acetate (50:50 by volume) and collecting fractions of 75 cm$^3$. Fractions 21 to 45 are combined and then concentrated to dryness under reduced pressure (2.7 kPa). 6.35 g of (3aRS,4RS,6SR,7aSR)-6-hydroxymethyl-4-(2-fluorophenyl)-2-tert-butyloxycarbonylperhydroisoindol 4-ol are obtained in the form of a thick white foam.

EXAMPLE 14

(3aRS,4RS,6SR,7aSR)-6-Cyanomethyl-4-(2-fluorophenyl)-2-(2-hydroxyphenylacetyl) perhydroisoindol-4-ol The procedure is as described for Example 13, starting from 1.67 g of (3aRS,4RS,6RS,7aSR)-6-p-toluenesulphonyloxymethyl-4-(2-fluorophenyl)-2-(2-benzyloxyphenylacetyl)perhydroisoindol-4-ol and 0.104 g of potassium cyanide, and gives 0.35 g of (3aRS,4RS,6SR,7aSR)-6-cyanomethyl-4-(2-fluorophenyl)-2-(2-benzyloxyphenylacetyl)perhydroisoindol-4-ol in the form of a thick pink foam.

0.032 g of 10% palladium hydroxide on carbon is added to a solution of 0.168 g of (3aRS,4RS,6SR,7aSR)-6-cyanomethyl-4-(2-fluorophenyl)-2-(2-benzyloxyphenylacetyl)perhydroisoindol-4-ol in 10 cm$^3$ of absolute ethanol, and then the reaction mixture is hydrogenated at reflux with stirring. After reaction for 4 hours, the reaction mixture is filtered and then concentrated to dryness under reduced pressure (2.7 kPa). Trituration in diisopropyl ether gives 0.08 g of (3aRS,4RS,6SR,7aSR)-6-cyanomethyl-4-(2-fluorophenyl)-2-(2-hydroxyphenylacetyl)perhydroisoindol-4-ol in the form of a thick white foam.

$^1$H NMR spectrum (400 MHz, (CD$_3$)$_2$SO d6, at a temperature of 403 K, δ in ppm): 1.60 and 1.98 (m and broad d respectively (J=14 Hz), each 1H: CH$_2$ 7); 1.89 and 2.05 (broad d (J=14 Hz) and m, respectively, each 1H: CH$_2$ 5); 2.40 to 2.60 (m, 3H: H 6 and CH$_2$CN); 2.50 to 2.90 (m, 23: H 7a and H3a); 3.10 to 3.80 (m, 6H: NCH$_2$ and CH$_2$Ar); 4.80 (unresolved, spread-out multiplet: OH): 6.75 to 7.70 (m, 83: aromatic H).

Infrared spectrum (characteristic bands in cm$^{-1}$): 3430, 3080+3040, 2925, 2890, 2855, 2790+2745+2640, 2250, 1625, 1600+1490+1485, 1460, 1255, 1210, 1100, 1040, 970, 760.

(3aRS,4RS,6SR,7aSR)-6-p-Toluenesulphonyloxymethyl-4-(2-fluorophenyl)-2-(2-benzyloxyphenylacetyl) perhydroisoindol-4-ol can be prepared as follows:

The procedure is as described for Example 13, starting from 0.72 g of (3aRS,4RS,6SR,7aSR)-6-hydroxymethyl-4-(2-fluorophenyl)-2-(2-benzyloxyphenylacetyl) perhydroisoindol-4-ol, 0.55 g of p-toluenesulphonyl chloride and 0.4 cm$^3$ of triethylamine, and gives, after purification on a silica gel column (particle size 0.04–0.06 mm, diameter 2.4 cm, height 20 cm), eluting under a pressure of 0.5 bar of nitrogen with a mixture of cyclohexane and ethyl acetate (50:50 by volume), 0.51 g of (3aRS,4RS,6SR,7aSR)-6-p-toluenesulphonyloxymethyl-4-(2-fluorophenyl)-2-(2-benzyloxyphenylacetyl) perhydroisoindol-4-ol in the form of a thick white foam.

(3aRS,4RS,6SR,7aSR)-6-Hydroxymethyl-4-(2-fluorophenyl)-2-(2-benzyloxyphenylacetyl) perhydroisoindol-4-ol can be prepared as follows:

0.54 g of carbonyldiimidazole is added to a solution of 0.8 g of 2-benzyloxyphenylacetic acid in 10 cm$^3$ of dichloromethane, cooled to 0° C. The mixture is stirred at this temperature for 2 hours and then 0.8 g of (3aRS,4RS,6SR,7aSR)-6-hydroxymethyl-4-(2-fluorophenyl) perhydroisoindol-4-ol hydrochloride and 1.04 cm$^3$ of diisopropylethylamine are added. The reaction mixture is stirred at room temperature for 18 hours, and then the organic phase is washed with 10 cm$^3$ of water, then with 10 cm$^3$ of saturated aqueous sodium chloride solution, dried over magnesium sulphate and concentrated to dryness under reduced pressure (2.7 kPa). The residue is chromatographed on a silica gel column (particle size 0.04–0.06 mm, diameter 3.2 cm, height 20 cm), eluting under a pressure of 0.5 bar of nitrogen with ethyl acetate and collecting fractions of 25 cm$^3$. Fractions 18 to 50 are combined and then concentrated to dryness under reduced pressure (2.7 kPa). 0.72 g of (3aRS,4RS,6SR,7aSR)-6-hydroxymethyl-4-(2-fluorophenyl)-2-(benzyloxyphenylacetyl)perhydroisoindol-4-ol is obtained in the form of a thick white foam.

EXAMPLE 15

(3aRS,4RS,6SR,7aSR)-6-Cyanomethyl-4-(2-fluorophenyl)-2-[2-(1-pyrrolidinyl)phenylacetyl] perhydroisoindol-4-ol The procedure is as described for Example 13, starting from 0.07 g of (3aRS,4RS,6SR,7aSR)-6-p- toluenesulphonyloxymethyl-4-(2-fluorophenyl)-2-[2-(1-pyrrolidinyl)phenylacetyl]perhydroisoindol-4-ol and 0.015 g of potassium cyanide, and gives 0.024 g of (3aRS,4RS,6SR,7aSR)-6-cyanomethyl-4-(2-fluorophenyl)-2-[2-(1-pyrrolidinyl)phenylacetyl]perhydroisoindol-4-ol in the form of a thick white foam.

$^1$H NMR spectrum (400 MHz, (CD$_3$)$_2$SO d6 with addition of a few drops of CD$_3$COOD-d$_4$, at a temperature of 413 K, δ in ppm): 1.58 (d, J=14 and 6 Hz, 1H: 1H of CH$_2$ 7); 1.80 to 2.00 (m, 6H: the other H of CH$_2$ 7–1H of CH$_2$ 5 and CH$_2$ of the pyrrolidine); 2.03 (broad t, J=13 Hz, 1H: the other H of CH$_2$ 5); 2.45 to 2.55 (m, 3H: H 6 and CH$_2$CN); 2.50 to 2.70 (m, 2H: H 7a and H 3a); 3.04 (m, 4H: NCH$_2$ of the pyrrolidine); 3.00 to 3.70 (m, 6H: NCH$_2$ and CH$_2$Ar); 6.75 to 7.70 (m, 8H: aromatic H).

Infrared spectrum (characteristic bands in cm$^{-1}$): 3430, 3070+3030, 2970+2930, 2880, 2860, 2825, 2250, 1625, 1605+1585+1495+1485, 1455, 1210, 1100, 1010, 970, 765.

(3aRS,4RS,6SR,7aSR)-6-p-Toluenesulphonyloxymethyl-4-(2-fluorophenyl)-2-[2-(1-pyrrolidinyl)phenylacetyl]perhydroisoindol-4-ol can be prepared as follows:

The procedure is as described for Example 13, starting from 0.2 g of (3aRS,4RS,6SR,7aSR)-6-hydroxymethyl-4-(2-fluorophenyl)-2-[2-(1-pyrrolidinyl)phenylacetyl]perhydroisoindol-4-ol, 0.168 g of p-toluenesulphonyl chloride and 0.124 cm$^3$ of triethylamine, and gives 0.07 g of (3aRS,4RS,6SR,7aSR)-6-p-toluenesulphonyloxymethyl-4-(2-fluorophenyl)-2-[2-(1-pyrrolidinyl)phenylacetyl]perhydroisoindol-4-ol in the form of a thick white foam.

(3aRS,4RS,6SR,7aSR)-6-Hydroxymethyl-4-(2-fluorophenyl)-2-[2-(1-pyrrolidinyl)phenylacetyl]perhydroisoindol-4-ol can be prepared as follows:

The procedure is as described for Example 14, starting from 0.73 g of (3aRS,4RS,6SR,7aSR)-6-hydroxymethyl-4-(2-fluorophenyl)perhydroisoindol-4-ol hydrochloride and 0.68 g of 2-(1-pyrrolidinyl)phenylacetic acid, and gives 0.2 g of (3aRS,4RS,6SR,7aSR)-6-hydroxymethyl-4-(2-fluorophenyl)-2-[2-(1-pyrrolidinyl)phenylacetyl]perhydroisoindol-4-ol in the form of a thick white foam.

EXAMPLE 16

(3aS,4S,6R,7aR)-6-Azidomethyl-4-(2-methoxyphenyl)-2-[(S)-2-(2-methoxyphenyl)propionyl]perhydroisoindol-4-ol:

1.68 g of sodium azide are added to a solution, which has been brought to 50° C., of 9.0 g of (3aS,4S,6R,7aR)-4-(2-methoxyphenyl)-2-[(S)-2-(2-methoxyphenyl)propionyl]-6-tosyloxymethylperhydroisoindol-4-ol in 50 cm$^3$ of dimethylformamide. The reaction mixture is stirred at 20° C. for 20 hours and then diluted with 350 cm$^3$ of water and subjected to extraction with 100 cm$^3$ of ethyl acetate. The organic phase is washed with 100 cm$^3$ of water, dried over magnesium sulphate and then concentrated to dryness under reduced pressure (2.7 kPa). 7.0 g of (3aS,4S,6R,7aR)-6-azidomethyl-4-(2-methoxyphenyl)-2-[(S)-2-(2-methoxyphenyl)propionyl]perhydroisoindol-4-ol are obtained in the form of a thick white foam.

$^1$H NMR spectrum (400 MHz, (CD$_3$)$_2$SO d6, δ in ppm): (at room temperature the rotamer mixture is observed). 1.16 and 1.22 (2 d, J=7 Hz, 3H: CH$_3$); 1.38 (m, 1H: 1H of CH$_2$ 7); 1.44 and 1.60 (2 broad d, J=13 Hz, 1H in all: 1H of CH$_2$ 5); 1.75 and 1.83 (2 broad d, J=14 Hz, 1H in all: the other H of CH$_2$ 7); 2.20 to 2.35 (m, 2H: the other H of CH$_2$ 5 and H 6); 2.37 and 2.49 (2 m, 1H: H 7a); 2.61 and 2.75 (2 m, 1H: H 3a); 2.90 to 3.70 (m, 4H: NCH$_2$); 3.21 (m, 2H: CH$_2$N); 3.59–3.76–3.80 and 3.85 (4s, 6H in all: OCH$_3$); 3.96 and 4.11 (2 q, J=7 Hz, 1H in all: ArCH); 4.19 and 4.80 (2 broad s, 1H in all: OH); 6.65 to 7.65 (m, 8H: aromatic H).

EXAMPLE 17

(3aRS,4RS,6SR,7aSR)-6-Azidomethyl-4-(2-methoxyphenyl)-2-[(2-methoxyphenyl)acetyl]perhydroisoindol-4-ol 0.35 g of sodium azide is added to a solution of 2.03 g of (3aRS,4RS,6SR,7aSR)-4-(2-methoxyphenyl)-2-[(2-methoxyphenyl)acetyl]-6-tosylmethylperhydroisoindol-4-ol in 10 cm$^3$ of dimethylformamide. The reaction mixture is heated at 50° C. for 8 hours and stirred at 20° C. for 48 hours and then diluted with 150 cm$^3$ of water and subjected to extraction twice with 40 cm$^3$ of ethyl acetate. The organic phase is washed with 50 cm$^3$ of water, dried over magnesium sulphate and then concentrated to dryness under reduced pressure (2.7 kPa). 1.6 g of (3aRS,4RS,6SR,7aSR)-6-azidomethyl-4-(2-methoxyphenyl)-2-[(2-methoxyphenyl)acetyl]perhydroisoindol-4-ol are obtained in the form of a thick white foam.

$^1$H NMR spectrum (250 MHz, (CD$_3$)$_2$SO d6 with addition of a few drops of CD$_3$COOD-d$_4$, at a temperature of 393 K, δ in ppm): coalescence is not total, and some instances of splitting will still be observed owing to the mixture of rotamers. 1.48 and 1.90 (d and broad d respectively, J=14 and 6 Hz and J=14 Hz, each 1H: CH$_2$ 7); 1.70 and 2.22 (m and broad t respectively (J=13 Hz, each 1H: CH$_2$ 5); 2.30 to 2.50 (m, 1H: H 6); 2.50 to 2.75 (m, 1H: H 7a); 2.86 (m, 1H: H 3a); 3.00 to 3.80 (m, 6H: NCH$_2$ and CH$_2$Ar); 3.26 (d, J=6 Hz, 2H: CH$_2$N); 3.70 to 3.81 (2 broad s, 3H in all: OCH$_3$); 3.85 (s, 3H: OCH$_3$); 6.85 to 7.65 (m, 8H: aromatic H).

Infrared spectrum (KBr), characteristic bands (cm$^{-1}$): 3400, 3070, 2925, 2880, 2835, 2095, 1625, 1600+1580+1495+1480, 1460, 1435, 1285, 1245+1235, 1105, 1050, 1030, 960, 755.

(3aRS,4RS,6SR,7aSR)-4-(2-Methoxyphenyl)-2-[(2-methoxyphenyl)acetyl]-6-tosylmethylperhydroisoindol-4-ol can be prepared as follows:

3.05 g of p-toluenesulphonyl chloride are added to a solution of 3.4 g of (3aRS,4RS,6SR,7aSR)-6-hydroxymethyl-4-(2-methoxyphenyl)-2-[(2-methoxyphenyl)acetyl]perhydroisoindol-4-ol and 2.24 cm$^3$ of triethylamine in 150 cm$^3$ of dichloromethane. The mixture is stirred at 20° C. for 20 hours, washed with 100 cm$^3$ of water, dried over magnesium sulphate and then concentrated to dryness under reduced pressure (2.7 kPa). 4.1 g of (3aRS,4RS,6SR,7aSR)-4-(2-methoxyphenyl)-2-[(2-methoxyphenyl)acetyl]-6-tosylmethylperhydroisoindol-4-ol are obtained in the form of a thick white foam.

$^1$H NMR spectrum (250 MHz, (CD$_3$)$_2$SO d6 with the addition of a few drops of CD$_3$COOD-d$_4$, at a temperature of 393 K, δ in ppm): 1.45 and 1.80 (d and broad d respectively, J=14 and 5.5 Hz and J=14 Hz, each 1H: CH$_2$ 7); 1.60 and 2.12 (broad d and t respectively, J=13 Hz, each 1H: CH$_2$ 5); 2.41 (s, 3H: ArCH$_3$); 2.35 to 2.70 (m, 2H: H 6 and H 7a); 2.82 (m, 1H: H 3a); 3.00 to 3.65 (m, 6H: NCH$_2$ and CH$_2$Ar); 3.75 (broad s, 3H: OCH$_3$); 3.81 (s, 3H: OCH$_3$); 4.00 (m, 2H: CH$_2$O); 6.85 to 7.65 (m, 8H: aromatic H); 7.45 and 7.78 (2 d, J=7.5 Hz, each 2H: aromatic H of the tosyl).

(3aRS,4RS,6SR,7aSR)-6-Hydroxymethyl-4-(2-methoxyphenyl)-2-[(2-methoxyphenyl)acetyl]perhydroisoindol-4-ol can be prepared as follows:

2.3 g of 1-(3-dimethylaminopropyl)-3-ethylcarbodiimide hydrochloride are added to a solution of 3 g of (3aRS,4RS, 6SR,7aSR)-6-hydroxymethyl-4-(2-methoxyphenyl) perhydroisoindol-4-ol and 1.8 g of (2-methoxyphenyl)acetic acid in 60 cm³ of dichloromethane. The reaction mixture is stirred at 20° C. for 20 hours and then washed with 30 cm³ of water, dried over magnesium sulphate and concentrated to dryness under reduced pressure (2.7 kPa). The residue is chromatographed on a silica gel column (particle size 0.06–0.20 mm, height [lacuna]cm) in ethyl acetate and then in a mixture of ethyl acetate and methanol (95:5 by volume). Drying under reduced pressure gives a white solid which, after recrystallization from a mixture of ethyl ether and acetonitrile, gives 2.1 g of (3aRS,4RS,6SR,7aSR)-6-hydroxymethyl-4-(2-methoxyphenyl)-2-[(2-methoxyphenyl)acetyl]perhydroisoindol-4-ol in the form of white crystals. M.p.=162° C.

NMR (DMSO-$d_6$+AcOD, 250 MHz, T=403° K.), δ (ppm): 1.42 and 1.85 (m and d, 2×1H, CH-C$\underline{H}_2$—CH), 1.69 and 2.04 (d and t, 2×1H, C—C$\underline{H}_2$—CH), 2.17 (m, 1H, C$\underline{H}$—CH$_2$OH), 2.57 (m, 1H, CH$_2$—C$\underline{H}$—CH), 2.85 (t, 1H, CH—C$\underline{H}$—C), 3.17 and 3.40 (m and d, 2×1H, —N—C$\underline{H}_2$—CH), 3.35 (d, 2H, O—C$\underline{H}_2$—CH), 3.47 (s, 2H, CO—C$\underline{H}_2$—Ph), 3.49 (m, 2H, N—C$\underline{H}_2$—CH), 3.75 (s, 3H, OC$\underline{H}_3$), 3.82 (s, 3H, OCH$_3$), 6.80–7.55 (8H, aromatic).

Infrared spectrum (KBr), characteristic bands (cm$^{-1}$): 3430, 3075, 3000–2875, 2835, 1620, 1605, 1495, 1485, 1460, 1435, 1245, 1055, 1030, 750.

EXAMPLE 18

(3aRS,4RS,6SR,7aSR)-6-Cyanoaminomethyl-4-(2-methoxyphenyl)-2-[(2-methoxyphenyl)acetyl] perhydroisoindolol:

0.25 g of cyanogen bromide is added to a solution of 1.0 g of (3aRS,4RS,6SR,7aSR)-6-aminomethyl-4-(2-methoxyphenyl)-2-[(2-methoxyphenyl)acetyl] perhydroisoindolol in 10.0 cm³ of anhydrous tetrahydrofuran. The mixture is stirred at 20° C. for 20 hours and then concentrated to dryness at 40° C. under reduced pressure (2.7 kPa). The residue obtained is chromatographed on a silica gel column (particle size 0.04–0.063 mm, diameter 2.0 cm, height 47 cm), eluting under a pressure of 0.5 bar of nitrogen with a mixture of cyclohexane and ethyl acetate (30:70 by volume) and collecting fractions of 25 cm³. Fractions 31 to 42 are concentrated to dryness to give 0.20 g of (3aRS,4RS,6SR,7aSR)-6-cyanoaminomethyl-4-(2-methoxyphenyl)-2-[ (2-methoxyphenyl)acetyl]isoindol-4-ol in the form of a white solid.

$^1$H NMR spectrum (400 MHz, (CD$_3$)$_2$SO d6 with addition of a few drops of CD$_3$COOD-d$_4$, at a temperature of 393 K, δ in ppm): 1.45 and 1.92 (d and broad d, respectively, J=14 and 6 Hz and J=14 Hz, each 1H: CH$_2$ 7); 1.73 and 2.12 (broad d and broad t respectively, J=13 Hz, each 1H: CH$_2$ 5); 2.33 (m, 1H: H 6); 2.62 (m, 1H: H 7a); 2.86 (m, 3H: H 3a and CH$_2$N); 3.10 to 3.80 (m, 6H: NCH$_2$ and CH$_2$Ar); 3.75 (unresolved multiplet, 3H: OCH$_3$); 3.85 (s, 3H: OCH$_3$); 6.85 to 7.65 (m, 8H: aromatic H).

Infrared spectrum (KBr), characteristic bands (cm$^{-1}$): 3410, 3200, 3070, 2925, 2880, 2840, 2215, 1620, 1600+1490+1480, 1460, 1435, 1285, 1245+1235, 1105, 1050, 1030, 960, 755.

(3aRS,4RS,6SR,7aSR)-6-Aminomethyl-4-(2-methoxyphenyl)-2-[(2-methoxyphenyl)acetyl] perhydroisoindol-4-ol can be prepared as follows:

A mixture of 6.05 g of (3aRS,4RS,6SR,7aSR)-6-azidomethyl-4-(2-methoxyphenyl)-2-[(2-methoxyphenyl) acetyl]perhydroisoindol-4-ol, 0.6 g of 10% palladium on carbon and 300 cm³ of ethanol is heated to 60° C. Hydrogen is bubbled through for 3 hours, and then the reaction mixture is left at 20° C. for 20 hours and then purged with a stream of nitrogen, filtered and concentrated under reduced pressure (2.7 kPa). 5.7 g of (3aRS,4RS,6SR,7aSR)-6-aminomethyl-4-(2-methoxyphenyl)-2-[ (2-methoxyphenyl)acetyl] perhydroisoindol-4-ol are obtained in the form of a thick white foam.

$^1$H NMR spectrum (250 MHz, (CD$_3$)$_2$SO d6 with addition of a few drops of CD$_3$COOD-d$_4$, at a temperature of 393 K, δ in ppm): 1.47 and 1.95 (d and broad d respectively, J=14 and 6 Hz and J=14 Hz, each 1H: CH$_2$ 7); 1.81 and 2.15 (broad d and t respectively, J=13 Hz, each 1H: CH$_2$ 5); 2.35 to 2.55 (m, 1H: H 6); 2.55 to 2.75 (m, 1H: H 7a); 2.75 (m, 2H: CH$_2$N); 2.90 (m, 1H: H 3a); 3.10 to 3.80 (m, 6H: NCH$_2$ and CH$_2$Ar); 3.75 (broad s, 3H: OCH$_3$); 3.85 (s, 3H: OCH$_3$); 6.85 to 7.65 (m, 8H: aromatic H).

Infrared spectrum (KBr), characteristic bands (cm$^{-1}$): 3400, 3100+3070, 2940+2925, 2880, 2840, 2245, 1635, 1600+1585+1590+1495+1490, 1460+1435, 1245, 1110, 1055, 1030, 965, 755.

EXAMPLE 19

(3aS,4S,6R,7aR)-6-Fluoromethyl-4-(2-methoxyphenyl)-2-(S)-2-(2-methoxyphenyl) propionyl]perhydroisoindol-4-ol (diastereoisomer form A)

0.24 g of potassium fluoride is added to a solution of 0.5 g of (3aS,4S,6R,7aR)-4-(2-methoxyphenyl)-2-(S)-2-(2-methoxyphenyl)propionyl]-6-tosyloxymethylperhydroisoindol-4-ol in 15 cm³ of diethylene glycol and 3 cm³ of methanol. The reaction mixture is stirred at 60° C. for 20 hours and then at 85° C. for 24 hours and then cooled to 20° C., and subsequently 50 cm³ of water and 30 cm³ of ethyl acetate are added. The organic phase is withdrawn and the aqueous phase is reextracted with 10 cm³ of ethyl acetate. The combined organic extracts are subsequently washed with 20 cm³ of brine, dried over magnesium sulphate and then concentrated to dryness under reduced pressure (2.7 kPa). The residue is chromatographed on a silica gel column (particle size 0.04–0.063 diameter 1.5 cm, height 35 cm), eluting under a pressure of 0.1 bar of nitrogen with a mixture of cyclohexane and ethyl acetate (70:30 by volume) and collecting fractions of 25 cm³. Fractions 15 to 22 are concentrated to dryness and the residue is then solidified in diisopropyl ether. Filtration and drying under reduced pressure (2.7 kPa) give 50 mg of (3aS,4S,6R,7aR)-6-fluoromethyl-4-(2-methoxyphenyl)-2-(S)-2-(2-methoxyphenyl)propionyl]perhydroisoindol-4-ol (diastereoisomer form A) in the form of a white solid.

$^1$H NMR spectrum (250 MHz, (CD$_3$)$_2$SO d6 with addition of a few drops of CD$_3$COOD-d$_4$, at a temperature of 393 K, δ in ppm): 1.28 (d, J=7 Hz, 3H: CH$_3$); 1.50 and 1.82 (m and broad d respectively (J=14 Hz), each 1H: CH$_2$ 7); 1.65 and 2.21 (m and t respectively (J=13 Hz), each 1H: CH$_2$ 5); 2.30 to 2.60 (m, 2H: H 6 and H 7a); 2.80 (m, 1H: H 3a); 3.00 to 3.90 (m, 4H: NCH$_2$); 3.60 to 3.90 and 3.82 (unresolved multiplier and s, respectively, 6H in all: OCH$_3$); 4.10 (m, 1H: ArCH); 4.30 (dd, J=47.5 and 6 Hz, 2H: CH$_2$F); 6.80 to 7.30 (m, 8H: aromatic H).

Infrared spectrum (KBr), characteristic bands (cm$^{-1}$): 3560+3430, 3110+3070, 2970+2935, 2885, 2835, 1625, 1600+1585+1490, 1460+1435, 1250, 1105, 1060, 1030, 1020+1000, 960, 795, 755.

EXAMPLE 20

(3aRS,4RS,6SR,7aSR)-6-Bromomethyl-4-(2-methoxyphenyl)-2-[(2-methoxyphenyl)acetyl] perhydroisoindol-4-ol A solution of 1.16 g of (3aRS,4RS,6SR,7aSR)-4-(2-methoxyphenyl)-2-[(2-methoxyphenyl)acetyl]-6- tosylmethylperhydroisoindol-4-ol and 0.345 g of anhydrous lithium bromide in 60 cm³ of acetone is heated at reflux for 18 hours and then concentrated to reduced volume (10 cm3). Following the addition of 20 cm³ of water, the mixture is subjected to extraction with 40 cm³ of ethyl acetate, washed with 20 cm³ of water and then dried over magnesium sulphate. After concentration to dryness under reduced pressure (2.7 kPa), the residue is washed with 20 cm³ of ethyl ether, drained and dried under reduced pressure (2.7 kPa). 0.66 g of (3aRS,4RS,6SR,7aSR)-6-bromomethyl-4-(2-methoxyphenyl)-2-[(2-methoxyphenyl)acetyl]perhydroisoindol-4-ol is obtained in the form of a white solid. M.p.$_K$=191° C.

¹H NMR spectrum (400 MHz, (CD₃)SO-d₆, δ in ppm): (at room temperature, the rotamer mixture is observed). 1.48 and 1.96 (m and broad d respectively (J= 14 Hz), each 1H: CH₂ 7); 1.63 and 2.25 to 2.45 (2 m, each 1H: CH₂ 5); 2.25 to 2.45 (m, 1H: H 6); 2.55 and 2.63 (2 m, 1H in all: H 7a); 2.80 and 2.85 (2 m, 1H in all: H 3a); 2.90 to 3.70 (m, 8H: NCH₂—CH₂Ar and CH₂Br); 3.70–3.78–3.80 and 3.82 (4 s, 6H in all: OCH₃); 4.88 (m, 1H: OH); 6.85 to 7.65 (m, 8H: aromatic H).

Infrared spectrum (KBr), characteristic bands (cm⁻¹): 3420, 3340, 3070+3050+3030+3010, 2990, 2970+2940+2920, 2900+2880, 2860, 2840, 1630, 1600+1500+1485, 1460+1440, 1410, 1275+1230, 1250, 1110, 1050, 1030, 950, 755.

EXAMPLE 21

(3aS,4S,6S,7aR)-6-Cyanomethyl-4-(2-methoxyphenyl)-2-[(S)-2-phenylpropionyl]perhydroisoindol-4-ol can be prepared as follows 0.87 cm³ of diisopropylethylamine, 0.75 g of (S)-2-phenylpropionic acid, 0.02 g of hydroxybenzotriazole hydrate and 1.05 g of 1-(3-dimethylaminopropyl)-3-ethylcarbodiimide hydrochloride are added to a solution of 1.43 g of (3aS,4S,6S,7aR)-6-cyanomethyl-4-(2-methoxyphenyl)perhydroisoindol-4-ol in 20 cm³ of dichloromethane. The reaction mixture is stirred at 20° C. for 20 hours and then washed twice with 30 cm³ of water, dried over magnesium sulphate and then concentrated to dryness under reduced pressure (2.7 kPa). The residue obtained is chromatographed on a silica gel column (particle size 0.04–0.063 mm, height 32 cm, diameter 2.8 cm), eluting under a pressure of 0.6 bar of nitrogen with a mixture of cyclohexane and ethyl acetate (50:50 by volume) and collecting fractions of 25 cm³. Fractions 19 to 35 are concentrated to dryness under reduced pressure (2.7 kPa). 1.20 g of (3aS,4S,6S,7aR)-6-cyanomethyl-4-(2-methoxyphenyl)-2-[(S)-2-phenylpropionyl]perhydroisoindol-4-ol in the form of a thick white foam are obtained.

¹H NMR spectrum in DMSO+AcOD, T=393 K, δ in ppm (250 MHz): 1.33 (3H, d, J=6 Hz, CH₃), 1.51 and 1.90 (each 1H, m, CH₂), 1.70 and 2.27 (each 1H, m, CH₂), 2.40 (3H, m, CH₂CN and CH), 2.53 (1H, m, CH), 2.78 (1H, t, J=6 Hz, CH), between 3.0 and 3.6 (4H, m, 2×NCH₂), 3.77 (1H, m, CH), 3.82 (3H, s, OCH₃), between 6.7 and 7.7 (9H, m, aromatic H).

Infrared spectrum (KBr), characteristic bands (cm⁻¹): 3420, 3065+3030, 2975, 2935, 2250, 1635, 1605+1585+1490, 1240, 1030, 760, 705.

EXAMPLE 22

(3aS,4S,6S,7aR)-6-Cyanomethyl-2-[(2-fluorophenyl) acetyl]-4-(2-methoxyphenyl)perhydroisoindol-4-ol can be prepared by proceeding as described in Example 21, from 0.32 g of (3aS,4S,6S,7aR)-6-cyanomethyl-4-(2-methoxyphenyl)-perhydroisoindol-4-ol hydrochloride, 25 cm³ of dichloromethane, 0.155 g of (4-fluorophenyl)acetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50, then pure ethyl acetate) gives 0.24 g of (3aS,4S,6S,7aR)-6-cyanomethyl-2-[(2-fluorophenyl)acetyl]-4-(2-methoxyphenyl)perhydroisoindol-4-ol in the form of a thick white foam.

¹H NMR spectrum in DMSO+CD₃CO₂D, T=300 K, δ in ppm (400 MHz): 50:50 mixture of the two rotamers: 1.50 and 1.90(each 1H, respectively m and d, J=16 Hz, CH₂), 1.63 and 2.38 (each 1H, respectively: t, J=10 Hz and m, CH₂), between 2.35 and 2.70 (4H, m, 2 CH and CH₂CN), 2.80/2.89 (1H, t, J=6 Hz, CH), between 2.95 and 3.70 (6H, m, 2 CH₂N and COCH₂Ph), 3.83 (3H, s, OCH₃), 4.95 (1H, s, OH), between 6.90 and 7.60 (8H, m, aromatic H).

Infrared spectrum (KBr), characteristic bands (cm⁻¹): 3600, 3250, 3069, 2941; 2884; 2853, 2838, 2243, 1631, 1583; 1493; 1455; 1437, 1455, 1233, 1027, 757.

EXAMPLE 23

(3aS,4S,6S,7aR)-6-Cyanomethyl-4-(2-methoxyphenyl)-2-[(2-tolyl)acetyl]perhydroisoindol-4-ol can be prepared by proceeding as described in Example 21, starting from 0.32 g of (3aS,4S,6S,7aR)-6-cyanomethyl-4-(2-methoxyphenyl) perhydroisoindol-4-ol hydrochloride, 25 cm³ of dichloromethane, 0.147 g of orthotolylacetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50, then with pure ethyl acetate) gives 0.250 g of (3aS,4S,6S,7aR)-6-cyanomethyl-4-(2-methoxyphenyl)-2-[(2-tolyl)acetyl]perhydroisoindol-4-ol in the form of a thick white foam.

¹H NMR spectrum in DMSO+CD₃CO₂D, T=300 K, δ in ppm (300 MHz): 55:45 mixture of the two rotamers: 1.50 and 1.88 (each 1H, m, CH₂), 1.65 and 2.38 (each 1H, respectively: t, J=10 Hz and m, CH₂), 2.17/2.21 (3H, s, PhCH₃), between 2.35 and 2.70 (4H, m, 2 CH and CH₂CN), 2.80/2.87 (1H, t, J=6 Hz, CH), between 2.95 and 3.70 (6H, m, 2 CH₂N and COCH₂Ph), 3.80 (3H, s, OCH₃), 4.90 (1H, s, OH), between 6.90 and 7.60 (8H, m, aromatic H).

Infrared spectrum (KBr), characteristic bands (cm⁻¹): 3600+3250, 3070; 3020, 2945; 2885, 2838, 2243, 1630, 1581; 1485; 1453; 1438, 1453, 1235, 1027, 753.

EXAMPLE 24

(3aS,4S,6S,7aR)-6-Cyanomethyl-4-(2-methoxyphenyl)-2-[(3-thienyl)acetyl]perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ of dichloromethane, 0.140 g of 3-thienylacetic acid, 0.21 cm³ of diisopropylethylsmine, 0.01 g of hydroxybenzotriazole hydrate and 0.210 g of 1-(3- dimethylaminopropyl )-3-ethylcarbodiimide hydrochloride. Purification by chromatography (silica gel 0.06–0.200 mm, elution with a mixture of cyclohexane and ethyl acetate, 50:50 by volume) gives 0.18 g of (3aS,4S,6S,7aR)-6-cyanomethyl-4-(2-methoxyphenyl)-2-[(3-thienyl)acetyl]perhydroisoindol-4-ol in the form of a thick white foam.

¹H NMR spectrum in DMSO, T=300 K, δ in ppm (300 MHz): 50:50 mixture of the two rotamers: 1.50 and 1.89 (each 1H, respectively m and d, J=16 Hz, CH₂), 1.63 and 2.38 (each 1H, respectively: t, J=8 Hz and m, CH₂), between 2.35 and 2.70 (4H, m, 2 CH and CH₂CN), 2.78/2.87 (1H, t, J=6 Hz, CH), between 2.90 and 3.70 (6H, m, 2 CH₂N and CH₂CO), 3.80 (3H, s, OCH₃), 4.92 (1H, s, OH), between 6.85 and 7.65 (7H, m, aromatic H).

Infrared spectrum (KBr), characteristic bands (cm⁻¹): 3600, 3250, 3095; 3070, 2935; 2880, 2838, 2243, 1625, 1581; 1485; 1453; 1438, 1453, 1235, 1027, 758.

EXAMPLE 25

(3aS,4S,6S,7aR)-6-Cyanomethyl-2-[(S)-2-methoxy-2-phenylacetyl]-4-(2-methoxyphenyl)perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ of dichloromethane, 0.170 g of 2-methoxy-2-phenylacetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50) gives 0.180 g of (3aS,4S,6S,7aR)-6-cyanomethyl-2-[(S)-2-methoxy-2-phenylacetyl]-4-(2-methoxyphenyl)perhydroisoindol-4-ol in the form of a thick white foam.

¹H NMR spectrum in DMSO, T=300 K, δ in ppm (300 MHz): 55:45 mixture of the two rotamers: 1.44 and 1.84 (each 1H, m, CH₂), 1.49/1.61 and 2.34 (each 1H, m, CH₂), 2.44 (2H, m, CH₂CN), between 2.20 and 2.55 (2H, m, 2 CH), 2.68 (1H, t, J=4 Hz, CH), between 2.80 and 3.70 (4H, m, CH₂N), 3.75/3.77 (3H, s, OCH₃), 4.58/4.88 (1H, d, J=1 Hz, OH), 4.78/4.90 (1H, s, OH), between 6.75 and 7.60 (9H, m, aromatic H).

Infrared spectrum (KBr), characteristic bands (cm⁻¹): 3600, 3250, 3073; 3030, 2940; 2886; 2853, 2838, 2244, 1635, 1600; 1582; 1486; 1452; 1438, 1452, 1236, 1105, 1029, 759, 700.

EXAMPLE 26

(3aS,4S,6S,7aR)-6-Cyanomethyl-4-(2-methoxyphenyl)-2-[(2-thienyl)acetyl]perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ of dichloromethane, 0.14 g of 2-thienylacetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50 by volume, then with pure ethyl acetate) gives 0.24 g of (3aS,4S,6S,7aR)-6-cyanomethyl-4-(2-methoxyphenyl)-2-[(2-thienyl)acetyl]perhydroisoindol-4-ol in the form of a thick white foam.

¹H NMR spectrum in DMSO, T=300 K, δ in ppm (400 MHz): 50:50 mixture of the two rotamers: 1.52 and 1.90 (each 1H, respectively: m and t, J=16 Hz, CH₂), 1.64 and 2.38 (each 1H, respectively: t, J=8 Hz and m, CH₂), between 2.35 and 2.70 (4H, m, 2 CH and CH₂CN), 2.80/2.90 (1H, t, J=6 Hz, CH), between 2.95 and 3.70 (4H, m, 2 CH₂N), between 3.70 and 3.90 (2H, m, CH₂CO), 3.82 (3H, s, OCH₃), 4.88 (1H, s, OH), between 6.85 and 7.60 (7H, m, aromatic H).

Infrared spectrum (KBr), characteristic bands (cm⁻¹): 3600, 3250, 3105; 3070, 2930; 2885; 2839, 2244, 1633, 1581; 1485; 1453; 1438, 1453, 1236, 1027, 759.

EXAMPLE 27

(3aS,4S,6S,7aR)-6-Cyanomethyl-2-[(2,3-dimethoxyphenyl)acetyl]-4-(2-methoxyphenyl)perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ dichloromethane, 0.196 g of (2,3-dimethoxyphenyl)acetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate 50:50) gives 0.150 g of (3aS,4S,6S,7aR)-6-cyanomethyl-2-[(2,3-dimethoxyphenyl)acetyl]-4-(2-methoxylphenyl)perhydroisoindol-4-ol in the form of a thick white foam.

¹H NMR spectrum in DMSO, T=300 K, δ in ppm (300 MHz): 50:50 mixture of the two rotamers: 1.48 and 1.88 (each 1H, respectively: m and d, J=16 Hz, CH₂), 1.63 and 2.38 (each 1H, respectively: t, J=8 Hz and d, J=8 Hz, CH₂), between 2.35 and 2.45 (1H, m, CH), 2.50 (2H, m, CH₂CN), 2.42/2.62 (1H, m, CH), 2.77/2.86 (1H, t, J=6 Hz, CH), between 2.95 and 3.65 (6H, m, 2 CH₂N and PhCH₂CO), 3.64/3.70 (3H, s, OCH₃), 3.82 (6H, s, 2 OCH₃), 4.89 (1H, s, OH), between 6.70 and 7.55 (7H, m, aromatic H).

Infrared spectrum (KBr), characteristic bands (cm⁻¹): 3600, 3250, 3073, 2938; 2886, 2838, 2244, 1628, 2600; 1585; 1486; 1452; 1438, 1452, 1275; 1236, 1080; 1025; 1008, 759.

(2,3-dimethoxyphenyl)acetic acid can be prepared according to the method described by W. Wenner., J. Org. Chem, 548 (1950) incorporated herein by reference.

EXAMPLE 28

(3aS,4S,6S,7aR)-2-[(2-Chlorophenyl)acetyl]-6-cyanomethyl-4-(2-methoxyphenyl)perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ of dichloromethane, 0.17 g of (2-chlorophenylacetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50 by volume, then with pure ethyl acetate) gives 0.25 g of (3aS,4S,6S,7aR)-2-[(2-chlorophenyl)acetyl]-6-cyanomethyl-4-(2-methoxyphenyl)perhydroisoindol-4-ol in the form of a thick white foam.

¹H NMR spectrum in DMSO, T=300 K, δ in ppm (400 MHz): 50:50 mixture of the two rotamers: 1.52 and 1.92 (each 1H, respectively: m and t, J=16 Hz, CH₂), 1.66 and 2.40 (each 1H, respectively: t, J=8 Hz and m, CH₂), between 2.35 and 2.75 (4H, m, 2 CH and CH₂CN), 2.81/2.90 (1H, t, J=6 Hz, CH), between 2.95 and 3.80 (6H, m, 2 CH₂N and PhCH₂CO), 3.82 (3H, s, OCH₃), 4.90/4.92 (1H, s, OH), between 6.90 and 7.65 (8H, m, aromatic H).

Infrared spectrum (KBr), characteristic bands (cm⁻¹): 3600, 3250, 3068, 2939; 2883, 2838, 2243, 1630, 1598; 1581; 1484; 1453; 1438, 1553, 1235, 1027, 754.

EXAMPLE 29

(3aS,4S,6S,7aR)-6-Cyanomethyl-4-(2-methoxyphenyl)-2-phenylacetylperhydroisoindol-4-ol can be prepared by proceeding as described in Example 21, starting from 0.32 g of (3aS,4S,6S,7aR)-6-cyanomethyl-4-(2-methoxyphenyl) perhydroisoindol-4-ol hydrochloride, 25 cm³ of dichloromethane, 0.140 g of phenylacetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50) gives 0.240 g of (3aS,4S,6S,7aR)-6-cyanomethyl-4-(2-methoxyphenyl)-2-phenylacetylperhydroisoindol-4-ol in the form of a thick white foam.

¹H NMR spectrum in DMSO, T=300 K, δ in ppm (400 MHz): 50:50 mixture of the two rotamers: 1.50 and 1.88 (each 1H, respectively: m and d, J=12 Hz, CH₂), 1.64 and 2.38 (each 1H, respectively: dd, J=10 and 16 Hz and m, CH₂), between 2.30 and 2.45 (1H, m, CH), 2.50 (2H, m, CH₂CN), 2.57/2.63 (1H, m, CH), 2.78/2.85 (1H, t, J=6 Hz, CH), between 2.95 and 3.50 (4H, m, 2 CH₂N), between 3.50 and 3.75 (2H, m, PhCH₂CO), 3.80 (3H, s, OCH₃), 4.88/4.92 (1H, s, OH), between 6.90 and 7.60 (9H, m, aromatic H).

Infrared spectrum (KBr), characteristic bands (cm⁻¹): 3600, 3250, 3062; 3028, 2939; 2883; 2853, 2838, 2243, 1624, 1602; 1582; 1485; 1456; 1437, 1456, 1235, 1028, 758; 724, 697.

EXAMPLE 30

(3aS,4S,6S,7aR)-6-Cyanomethyl-2-[(3,4-dimethoxyphenyl)acetyl]-4-(2-methoxyphenyl) perhydroisoindol-4-ol can be prepared by proceeding as described in Example 21, starting from 0.32 g of (3aS,4S,6S,7aR)-6-cyanomethyl-4-(2-methoxyphenyl) perhydroisoindol-4-ol hydrochloride, 25 cm³ of dichloromethane, 0.200 g of (3,4-dimethoxyphenyl)acetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with pure ethyl acetate) gives 0.15 g of (3aS,4S,6S,7aR)-6-cyanomethyl-2-[(3,4-dimethoxyphenyl)acetyl]-4-(2-methoxyphenyl)perhydroisoindol-4-ol in the form of a thick white foam.

¹H NMR spectrum in DMSO, T=300 K, δ in ppm (300 MHz): 50:50 mixture of the two rotamers: 1.50 and 1.90 (each 1H, respectively: m and d, J=16 Hz, CH₂), 1.64 and 2.38 (each 1H, respectively: t, J=8 Hz and d, J=8 Hz, CH₂), between 2.35 and 2.70 (4H, m, 2 CH and CH₂CN), 2.77/2.82 (1H, t, J=6 Hz, CH), between 2.90 and 3.65 (6H, m, 2 CH₂N and PhCH₂CO), between 3.65 and 3.95 (9H, s, 3 OCH₃), 4.83/4.87 (1H, s, OH), between 6.65 and 7.60 (7H, m, aromatic H).

Infrared spectrum (KBr), characteristic bands (cm⁻¹): 3600, 3250, 3075, 2937; 2886, 2836, 2243, 1622, 1592; 1516; 1485; 1456; 1436, 1556, 1236, 1027, 788, 760.

EXAMPLE 31

(3aS,4S,6S,7aR)-6-Cyanomethyl-4-(2-methoxyphenyl)-2-[(2-trifluoromethylphenyl)acetyl]perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ of dichloromethane, 0.200 g of (2-trifluoromethylphenhyl)acetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50) gives 0.250 g of (3aS,4S,6S,7aR)-6-cyanomethyl-4-(2-methoxyphenyl)-2-[(2-trifluoromethylphenyl)acetyl]perhydroisoindol-4-ol in the form of a thick, light beige foam.

¹H NMR spectrum in DMSO, T=300 K, δ in ppm (400 MHz): 50:50 mixture of the two rotamers: 1.50 and 1.90 (each 1H, respectively: m and d, J=16 Hz, CH₂), 1.64 and 2.38 (each 1H, respectively: t, J=8 Hz and d, J=8 Hz, CH₂), between 2.35 and 2.45 (1H, m, CH), 2.50 (2H, m, CH₂CN), 2.57/2.68 (1H, m, CH), 2.80/2.88 (1H, t, J=6 Hz, CH), between 2.95 and 3.65 (4H, m, 2 CH₂N), 3.65/3.77 (2H, s, PhCH₂CO), 3.82 (3H, s, OCH₃), 4.95/4.96 (1H, s, OH), between 6.90 and 7.75 (8H, m, aromatic H).

Infrared spectrum (KBr), characteristic bands (cm⁻¹): 3600, 3250, 3073, 2925; 2886; 2853, 2838, 2244, 1632, 1582; 1486; 1452; 1438, 1452, 1315, 1236, 1158; 1118, 1029, 767; 759.

EXAMPLE 32

(3aS,4S,6S,7aR)-6-Cyanomethyl-4-(2-methoxyphenyl)-2-[(4-methoxyphenyl)acetyl]perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ of dichloromethane, 0.166 g of (4-methoxyphenyl) acetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50) gives 0.150 g of (3aS,4S,6S,7aR)-6-cyanomethyl-4-(2-methoxyphenyl)-2-[(4-methoxyphenyl)acetyl] perhydroisoindol-4-ol in the form of a thick white foam.

¹H NMR spectrum in DMSO, T=300 K, δ in ppm (300 MHz): 50:50 mixture of the two rotamers: 1.49 and 1.88 (each 1H, respectively: m and d, J=16 Hz, CH₂), 1.64 and 2.38 (each 1H, respectively: t, J=8 Hz and m, CH₂), between 2.35 and 2.70 (4H, m, 2 CH and CH₂CN), 2.77/2.82 (1H, t, J=6 Hz, CH), between 2.90 and 3.70 (6H, m, 2 CH₂N and PhCH₂CO), 3.75/3.77 (3H, s, OCH₃), 3.81/3.82 (3H, s, OCH₃), 4.85/4.92 (1H, s, OH), between 6.75 and 7.65 (8H, m, aromatic H).

Infrared spectrum (KBr), characteristic bands (cm⁻¹): 3600, 3250, 3070, 2937; 2884, 2836, 2243, 1620, 1582; 1513; 1485; 1454; 1438, 1454, 1245, 1030, 812, 757.

EXAMPLE 33

(3aS,4S,6S,7aR)-6-Cyanomethyl-4-(2-methoxyphenyl)-2-[(3-methoxyphenyl)acetyl]perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm³ of dichloromethane, 0.166 g of (3-methoxyphenyl) acetic acid, 0.21 cm³ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate 50:50) followed by recrystallization from acetonitrile gives 0.20 g of (3aS,4S,6S,7aR)-6-cyanomethyl-4-(2-methoxyphenyl)-2-[(3-methoxyphenyl)acetyl] perhydroisoindol-4-ol in the form of white crystals. M.p.ₖ= 152° C.

¹H NMR spectrum in DMSO, T=300 K, δ in ppm (300 MHz): 50:50 mixture of the two rotamers: 1.50 and 1.90

(each 1H, respectively: m and d, J=16 Hz, CH$_2$), 1.64 and 2.38 (each 1H, respectively: t, J=8 Hz and d, J=8 Hz, CH$_2$), between 2.35 and 2.70 (4H, m, 2 CH and CH$_2$CN), 2.79/2.85 (1H, t, J=6 Hz, CH), between 2.95 and 3.70 (6H, m, 2 CH$_2$N and PhCH$_2$CO), 3.75 (3H, s, OCH$_3$), 3.81/3.82 (3H, s, OCH$_3$), 4.90/4.95 (1H, s, OH), between 6.75 and 7.75 (8H, m, aromatic H).

Infrared spectrum (KBr), characteristic bands (cm$^{-1}$): 3600, 3250, 3053, 2939; 2885, 2836, 2243, 1625, 1600; 1583; 1489; 1454; 1438, 1454, 1235, 1028, 759.

EXAMPLE 34

(3aS,4S,6S,7aR)-6-Cyanomethyl-2-[(3-fluorophenyl)acetyl]-4-(2-methoxyphenyl)perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm$^3$ of dichloromethane, 0.155 g of (4-fluorophenyl)acetic acid, 0.21 cm$^3$ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50, then pure ethyl acetate) gives 0.20 g of (3aS,4S,6S,7aR)-6-cyanomethyl-2-[(3-fluorophenyl)acetyl]-4-(2-methoxyphenyl)perhydroisoindol-4-ol in the form of a thick white foam.

$^1$H NMR spectrum in DMSO+CD$_3$CO$_2$D, T=300 K, δ in ppm (300 MHz): 50:50 mixture of the two rotamers: 1.50 and 1.90 (each 1H, respectively: m and d, J=16 Hz, CH$_2$), 1.64 and 2.38 (each 1H, respectively: t, J=8 Hz and d, J=8 Hz, CH$_2$), between 2.35 and 2.70 (4H, m, 2 CH and CH$_2$CN), 2.80/2.87 (1H, t, J=6 Hz, CH), between 2.95 and 3.70 (6H, m, 2 CH$_2$N and PhCH$_2$CO), 3.80/3.81 (3H, s, OCH$_3$), between 6.85 and 7.65 (8H, m, aromatic H).

Infrared spectrum (KBr), characteristic bands (cm$^{-1}$): 3600, 3250, 3063, 2930; 2885, 2839, 2244, 1627, 1589; 1487; 1453; 1438, 1453, 1236, 1027, 759.

EXAMPLE 35

(3aS,4S,6S,7aR)-6-Cyanomethyl-2-[(4-fluorophenyl)acetyl]-4-(2-methoxyphenyl)perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm$^3$ of dichloromethane, 0.155 g of (4-fluorophenyl)acetic acid, 0.21 cm$^3$ of diisopropylethylamine, 0.01 g of hydroxybenzotriazole hydrate and 0.210 g of 1-(3-dimethylaminopropyl)-3-ethylcarbodiimide hydrochloride. Purification by chromatography (silica gel 0.06–0.200 mm, elution with a mixture of cyclohexane and ethyl acetate, 50:50, then pure ethyl acetate) gives 0.20 g of (3aS,4S,6S,7aR)-6-cyanomethyl-2-[(4-fluorophenyl)acetyl]-4-(2-methoxyphenyl)perhydroisoindol-4-ol in the form of a thick white foam.

$^1$H NMR spectrum in DMSO+CD$_3$CO$_2$D, T=300 K, δ in ppm (300 MHz): 50:50 mixture of the two rotamers: 1.50 and 1.88 (each 1H, respectively: m and d, J=16 Hz, CH$_2$), 1.64 and 2.39 (each 1H, respectively: t, J=8 Hz and d, J=8 Hz, CH$_2$), between 2.35 and 2.70 (4H, m, 2 CH and CH$_2$CN), 2.80/2.87 (1H, t, J=6 Hz, CH), between 2.95 and 3.70 (6H, m, 2 CH$_2$N and PhCH$_2$CO), 3.82 (3H, s, OCH$_3$), between 6.90 and 7.65 (8H, m, aromatic H).

Infrared spectrum (KBr), characteristic bands (cm$^{-1}$): 3600, 3250, 3070; 3050, 2931; 2885, 2840, 2244, 1624, 1582; 1510; 1485; 1454; 1437, 1554, 1234, 1027, 816, 758.

EXAMPLE 36

(3aS,4S,6S,7aR)-6-Cyanomethyl-2-[(3,4-difluorophenyl)acetyl]-4-(2-methoxyphenyl)perhydroisoindol-4-ol can be prepared by proceeding as described in Example 21, starting from 0.32 g of (3aS,4S,6S,7aR)-6-cyanomethyl-4-(2-methoxyphenyl)perhydroisoindol-4-ol hydrochloride, 25 cm$^3$ of dichloromethane, 0.17 g of (3,4-difluorophenyl)acetic acid, 0.21 cm$^3$ of diisopropylethylamine, 0.01 g of hydroxybenzotriazole hydrate and 0.21 g of 1-(3-dimethylaminopropyl)-3-ethylcarbodiimide hydrochloride. Purification by chromatography (silica gel 0.06–0.200 mm, elution with a mixture of cyclohexane and ethyl acetate, 40:60 then 20:80 by volume) gives 0.100 g of (3aS,4S,6S,7aR)-6-cyanomethyl-2-[(3,4-difluorophenyl)acetyl] -4-(2-methoxyphenyl)perhydroisoindol-4-ol in the form of a thick white foam.

$^1$H NMR spectrum in DMSO-d$_6$+CD$_3$CO$_2$D, T=300 K, d in ppm (300 MHz): 50:50 mixture of the two rotamers: 1.50 and 1.90 (1H, respectively m and d, J=16 Hz, CH$_2$), 1.63 and 2.38 (1H, respectively: t, J=10 Hz and m, CH$_2$), between 2.35 and 2.70 (4H, m, 2 CH and CH$_2$CN), 2.80/2.85 (1H, t, J=6 Hz, CH), between 2.95 and 3.70 (6H, m, 2 CH$_2$N and COCH$_2$Ph), 3.83 (3H, s, OCH$_3$), 4.90 (1H, s, OH), between 6.85 and 7.60 (7H, m, aromatic H).

Infrared spectrum (KBr), characteristic bands (cm$^{-1}$): 3600; 3250, 3072, 2940; 2880; 2850, 2838, 2243, 1625, 1581; 1515; 1485; 1453; 1437, 1453, 1235, 1028, 757.

EXAMPLE 37

(3aS,4S,6S,7aR)-6-Cyanomethyl-2-[(S)-2-hydroxy-2-phenylacetyl]-4-(2-methoxyphenyl)perhydroisoindol-4-ol can be prepared by proceeding as described in Example 1, starting from 1.4 g of (3aS,4S,6S,7aR)-6-cyanomethyl-4-(2-methoxyphenyl)perhydroisoindolol hydrochloride, 40 cm$^3$ of dichloromethane, 0.66 g of S-(+)-mandelic acid, 0.02 g of hydroxybenzotriazole hydrate, 0.88 cm$^3$ of diisopropylethylamine and 0.93 g of 1-(3-dimethylaminopropyl)-3-ethylcarbodiimide hydrochloride.

Purification by chromatography followed by recrystallization from ethyl acetate and drying at 45° C. under reduced pressure (2.7 kPa) give 1.17 g of (3aS,4S,6S,7aR )-6-cyanomethyl-2-[(S)-2-hydroxy-2-phenylacetyl]-4-(2-methoxyphenyl)perhydroisoindol-4-ol in the form of white crystals. M.p.$_K$=172° C.

EXAMPLE 38

(3aS,4S,6S,7aR)-6-Cyanomethyl-4-(2-methoxyphenyl)-2-[(R)-2-(2-methoxyphenyl)propionyl]-perhydroisoindol-4-ol can be prepared by proceeding as described in Example 5, starting from 0.57 g of (3aS,4S,6S,7aR)-6-cyanomethyl-4-(2-methoxyphenyl)perhydroisoindol-4-ol, 30 cm$^3$ of dichloromethane, 0.20 cm$^3$ of diisopropylamine, 0.36 g of (R)-2-(2-methoxyphenyl)propionic acid, prepared according to D. Matsumoto et al.: Bull. Chem. Soc. Jpn., 58, 340 (1985), incorporated herein by reference, 0.01 g of hydroxybenzotriazole hydrate and 0.42 g of 1-(3-dimethylaminopropyl)-3-ethylcarbodiimide hydrochloride. Purification by chromatography followed by drying under reduced pressure (2.7 kPa) give 0.40 g of (3aS,4S,6S,7aR)-6-cyanomethyl-4-(2-methoxyphenyl)-2-[(R)-2-(2-methoxyphenyl)propionyl]perhydroisoindol-4-ol in the form of a thick white foam.

$^1$H NMR spectrum in DMSO, T=300 K, δ in ppm (400 MHz): 40:60 mixture of the rotamers: 1.16 and 1.23 (3H, d, J=6 Hz, CH$_3$) , between 0.8 and 1.95 and at 2.35 (4H, m, 2

CH$_2$), 2.30 (1H, m, CH), 2.43 and 2.47 (2H, m, CNCH$_2$), 2.60 and 2.73 (1H, t, J=6 Hz, CH), between 2.90 and 3.60 (4H, m, NCH$_2$), at 3.60, 3.76, 3.80 and 3.85 (6H in total, s, OCH$_3$), 3.95 and 4.10 (1H, q, J=6 Hz, CH), 4.28 and 4.88 (1H, d, J=1 Hz, OH), between 6.65 and 7.65 (8 H in total, t or d, J=7 Hz, aromatic CH).

Infrared spectrum (KBr), characteristic bands (cm$^{-1}$): 3410, 3060, 2930, 2830, 2245, 1620, 1600+1580+1490, 1240, 1030, 755.

EXAMPLE 39

(3aS,4S,6S,7aR)-6-Cyanomethyl-4-(2-methoxyphenyl)-2-[(2-pyridyl)acetyl]perhydroisoindol-4-ol can be prepared by proceeding as described in Example 9, starting from 0.57 g of (3aS,4S,6S,7aR)-6-cyanomethyl-4-(2-methoxyphenyl) perhydroisoindol-4-ol, 30 cm$^3$ of dichloromethane, 0.35 g of 2-pyridylacetic acid, 0.36 cm$^3$ of diisopropylethylamine, 0.02 g of hydroxybenzotriazole hydrate and 0.42 g of 1-(3-dimethylaminopropyl )-3-ethylcarbodiimide hydrochloride. Purification by chromatography (silica gel 0.06–0.200 mm, elution with a mixture of 1,2-dichloroethane and methanol, 95:5) gives 0.40 g of (3aS, 4S,6S,7aR)-6-cyanomethyl-4-(2-methoxyphenyl)-2-[(2-pyridyl)acetyl]perhydroisoindol-4-ol in the form of a thick white foam.

$^1$H NMR spectrum in DMSO, T=300 K, δ in ppm (400 MHz): rotamer mixture: 1.50 and 1.88 (each 1H, respectively m and d, J=14 Hz, CH$_2$) , 1.63 and 2.37 (each 1H, m, CH$_2$), between 2.35 and 2.50 (3H, m, CH$_2$CN and CH), 2.55 and 2.63 (1H, m, CH), 2.79 and 2.90 (1H, t, J=6 Hz, CH), between 2.93 and 3.50 (4H, m, 2×NCH$_2$), between 3.55 and 3.80 (2H, m, COCH$_2$), 3.82 (3H, s, OCH$_3$), 4.94 and 4.96 (1H, s, OH), between 6.90 and 7.80 (7H, m, aromatic CH), 8.49 (1H, m, aromatic CH).

Infrared spectrum (KBr), characteristic bands (cm$^{-1}$): 3425, 3075, 2945, 2855, 2835, 2245, 1640, 1600+1570+1490, 1240, 1030, 760.

EXAMPLE 40

(3aS,4S,6S,7aR)-6-Cyanomethyl-4-(2-methoxyphenyl)-2-[(3-pyridyl)acetyl]perhydroisoindol-4-ol can be prepared by proceeding as described in Example 9, starting from 0.57 g of (3aS,4S,6S,7aR)-6-cyanomethyl-4-(2-methoxyphenyl) perhydroisoindol-4-ol, 30 cm$^3$ of dichloromethane, 0.35 g of 3-pyridylacetic acid, 0.35 cm$^3$ of diisopropylethylamine, 0.02 g of hydroxybenzotriazole hydrate and 0.40 g of 1-(3-dimethylaminopropyl)-3-ethylcarbodiimide hydrochloride. Purification by chromatography (silica gel 0.06–0.200 mm, elution with a mixture of 1,2-dichloroethane and methanol, 95:5) gives 0.37 g of (3aS, 4S,6S,7aR)-6-cyanomethyl-4-(2-methoxyphenyl)-2-[(3-pyridyl)acetyl]perhydroisoindol-4-ol in the form of a thick white foam.

$^1$H NMR spectrum in DMSO, T=300 K, δ in ppm (400 MHz): rotamer mixture: 1.50 and 1.90 (each respectively m and d, J=14 Hz, CH$_2$), 1.63 and 2.37 (each 1H, m, CH$_2$), between 2.35 and 2.50 (3H, m, CH$_2$CN and CH), 2.55 and 2.65 (1H, m, CH), 2.80 and 2.89 (1H, t, J=6 Hz, CH), between 2.95 and 3.55 (4H, m, 2×NCH$_2$), between 3.55 and 3.70 (2H, m, COCH$_2$), 3.81 (3H, s, OCH$_3$), 4.94 (1H, s, OH), between 6.90 and 7.70 (6H, m, aromatic CH), between 8.40 and 8.50 (2H, m, aromatic CH).

Infrared spectrum (KBr), characteristic bands (cm$^{-1}$): 3420, 3060+3030, 2945, 2850, 2840, 2245, 1640, 1600+1580+1485, 1240, 1030, 790, 760, 705.

EXAMPLE 41

(3aS,4S,6S,7aR)-6-Cyanomethyl-4-(2-methoxyphenyl)-2-{{2-[3-(1-pyrrolidinyl)propoxy]-phenyl}acetyl}perhydroisoindol-4-ol can be prepared by proceeding as described in Example 21, starting from 0.35 g of (3aS,4S,6S,7aR)-6-cyanomethyl-4-(2-methoxyphenyl) perhydroisoindol-4-ol, 25 cm$^3$ of dichloromethane, 0.22 cm$^3$ of diisopropylethylamine, 0.32 g of {2-[3-(1-pyrrolidinyl) propoxy]phenyl}acetic acid, 0.01 g of hydroxybenzotriazole hydrate and 0.26 g of 1-(3-dimethylaminopropyl)-3-ethylcarbodiimide hydrochloride. Purification by chromatography (silica gel 0.06–0.200 mm, column diameter 2.4 cm, height 27 cm, elution with a mixture of ethyl acetate and methanol, 50:50 by volume) gives 0.30 g of (3aS,4S,6S, 7aR)-6-cyanomethyl-4-(2-methoxyphenyl)-2-{{2-[3-(1-pyrrolidinyl)propoxy]phenyl}acetyl}perhydroisoindol-4-ol in the form of a thick white foam.

$^1$H NMR spectrum in DMSO+AcOD, T=403 K, δ in ppm (400 MHz): 1.57 and 1.95 (each 1H, respectively m and d, J=14 Hz, CH$_2$), 1.78 and 2.28 (each 1H, m, CH$_2$), 1.90 (4H, m, CH$_2$CH$_2$), 2.07 (2H, m, CH$_2$), between 2.40 and 2.50 (3H, m, CH$_2$CN and CH), 2.65 (1H, m, CH), 2.87 (1H, m, CH), between 3.0 and 3.15 (6H, m, 3×NCH$_2$), between 3.55 and 3.45 (2H, m, COCH$_2$), between 3.50 and 3.65 (4H, m, 2×NHC$_2$), 3.84 (3H, s, OCH$_3$), 4.09 (2H, m, OCH$_2$), 4.94 and 4.96 (1H, s, OH), between 6.85 and 7.60 (8H, m, aromatic CH).

Infrared spectrum (KBr), characteristic bands (cm$^{-1}$): 3425, 3070, 2955, 2800, 2245, 1630, 1600+1585+1485, 1235, 1050, 1025, 755.

{2-[3-(1-Pyrrolidinyl)propoxy]phenyl}acetic acid can be prepared as follows:

0.8 g of 10% palladium hydroxide on carbon is added to a solution of 5.3 g of benzyl {2-[3-(1-pyrrolidinyl)propoxy] phenyl}acetate in 50 cm$^3$ of ethyl acetate and 50 cm$^3$ of dichloromethane, and the mixture is heated to 50° C. and then purged with nitrogen. After hydrogen has been bubbled through for 20 hours, the suspension is cooled to room temperature and purged with a stream of nitrogen, then filtered and concentrated to dryness under reduced pressure (2.7 kPa). The oily residue obtained is chromatographed on an alumina column (particle size 100 mesh, height 30 cm, diameter 4.5 cm), eluting under a pressure of 0.7 bar of nitrogen with a mixture of cyclohexane and ethyl acetate (75:25 by volume) and collecting fractions of 100 cm$^3$. Fractions 1 to 6 are concentrated to dryness under reduced pressure (2.7 kPa). 2.9 g of {2-[3-(1-pyrrolidinyl)propoxy] phenyl}acetic acid are obtained in the form of a thick oil.

$^1$H NMR spectrum in CDCl$_3$, T=300 K, δ in ppm (250 MHz): 1.90 (4H, m, 2 CH$_2$), 2.10 (2H, m, CH$_2$), between 2.95 and 3.10 (6H, m, 3 CH$_2$N), 3.55 (2H, s, CH$_2$CO), 3.95 (2H, t, J=6 Hz, OCH$_2$), 6.78 (1H, d, J=7 Hz, aromatic H), 6.90 (1H, t, J=7 Hz, aromatic H), 7.16 (1H, t, J=7 Hz, aromatic H), 7.20 (1H, d, J=7 Hz, aromatic H), 11.15 (1H, s, COOH).

Infrared spectrum (CH$_2$Cl$_2$), characteristic bands (cm$^{-1}$): 2975; 2890, 2805, 1735, 1625, 1605; 1590; 1500; 1475; 1460, 1250.

Benzyl {2-[3-(1-pyrrolidinyl)propoxy]phenyl}acetate can be prepared as follows:

2.06 g of potassium carbonate, 0.5 g of sodium iodide and 1.25 cm$^3$ of pyrrolidine are added to a solution [lacuna] 5.3 g of benzyl [2-(3-bromopropoxy)phenyl)acetate in 100 cm$^3$ of acetonitrile. The mixture is heated at 90° C. for 3 hours and then cooled to room temperature, 50 cm$^3$ of water are added, and the mixture is then diluted with 50 cm³ of dichloromethane. The organic phase is separated off, washed with water and then dried over magnesium sulphate and concentrated to dryness under reduced pressure (2.7 kPa). 5.3 g of benzyl {2-[3-(1-pyrrolidinyl)propoxy] phenyl}acetate are obtained in the form of an orange-coloured oil.

¹H NMR spectrum in CDCl₃, T=300 K, δ in ppm (250 MHz): 1.80 (4H, m, 2 CH₂), 1.95 (2H, m, CH₂), 2.50 (4H, m, CH₂NCH₂), 2.60 (2H, t, J=6 Hz, CH₂N<), 3.70 (2H, s, CH₂CO), 4.02 (2H, t, J=6 Hz, OCH₂), 5.15 (2H, s, OCH₂Ph), between 6.80 and 7.40 (9H, m, aromatic H).

Benzyl [2-(3-bromopropoxy)phenyl]acetate can be prepared by the following procedure:

5.2 g of potassium carbonate and 40 cm³ of 1,3-dibromopropane are added to a solution of 4.84 g of benzyl [(2-hydroxy)phenyl]acetate in 100 cm³ of acetonitrile. The mixture is stirred at the reflux temperature for 20 hours and then cooled to room temperature before being filtered. The filtrate is concentrated to dryness under reduced pressure and the residue obtained is taken up in 200 cm³ of ethyl acetate. The solution is washed with twice 100 cm³ of water then with 150 cm³ of brine, and is dried over magnesium sulphate and concentrated under reduced pressure (2.7 kPa). The oil obtained is chromatographed on a silica gel column (particle size 0.06–0.200 height 30 cm, diameter 5 cm), eluting with a mixture of cyclohexane and ethyl acetate (95:5 by volume) and collecting fractions of 100 cm³. Fractions 18 to 28 are concentrated to dryness under reduced pressure (2.7 kPa). 2.0 g of benzyl [2-(3-bromopropoxy)phenyl]acetate are obtained in the form of an oil.

¹H NMR spectrum in CDCl₃, T=300 K, δ in ppm (250 MHz): 2.22 (2H, m, CH₂), 3.55 (2H, t, J=6 Hz, CH₂), 3.70 (2H, s, PhCH₂CO), 4.10 (2H, t, J=6 Hz, OCH₂), 5.20 (2H, s, OCH₂Ph), 6.90 (1H, d, J=7 Hz, aromatic H), 6.98 (1H, t, J=7 Hz, aromatic H), between 7.20 and 7.45 (7H, m, aromatic H).

Infrared spectrum (CCl₄), characteristic bands (cm⁻¹): 3100; 3075; 3040, 2955; 2940; 2885, 1745, 1605; 1590; 1500; 1460, 1250, 1150, 700.

Benzyl [(2-hydroxy)phenyl]acetate can be prepared by the following procedure:

A suspension of 22.6 g of 2-hydroxyphenylacetic acid, 0.5 g of paratoluenesulphonic acid in 15.5 cm³ of benzyl alcohol is heated at reflux for three hours. 2 g of 3S active carbon are added, the suspension is filtered over Supercel, and the filtrate is evaporated to dryness under reduced pressure (2.7 kPa). 30 g of benzyl [(2-hydroxy)phenyl]acetate are obtained in the form of crystals. M.p.$_K$=104° C.

The present invention also relates to the pharmaceutical compositions consisting of a product of general formula (I) or a salt, when they exist, optionally in combination with any other pharmaceutically compatible product, which may be inert or physiologically active. The compositions according to the invention may be used via the parenteral, oral, sublingual, rectal, topical, transdermal, ocular or intranasal route or as aerosols for the lungs.

The sterile compositions for parenteral administration which can be used in particular in the form of infusions are preferably aqueous or nonaqueous solutions, suspensions or emulsions. As solvent or vehicle it is possible to employ water, propylene glycol, a polyethylene glycol, vegetable oils, in particular olive oil, injectable organic esters, for example ethyl oleate, or other suitable organic solvents. These compositions can also contain adjuvants, in particular wetting agents, isotonicity agents, emulsifiers, dispersants and stabilizers. Sterilization may be achieved in a number of ways, for example by aseptic filtration, by incorporating sterilizing agents in the composition, by irradiation or by heating. They can also be prepared in the form of sterile solid compositions which can be dissolved at the time of use in an injectable sterile medium.

The compositions for rectal administration are suppositories or rectal capsules, which contain in addition to the active product excipients such as cocoa butter, semisynthetic glycerides or polyethylene glycols.

Solid compositions for oral administration which can be used are tablets, pills, powders or granules. In these compositions, the active product according to the invention (optionally combined with another pharmaceutically compatible product) is mixed with one or more inert adjuvants or diluents, such as sucrose, lactose or starch. These compositions can also comprise substances other than the diluents, for example a lubricant such as magnesium stearate.

Liquid compositions for oral administration which can be used are pharmaceutically acceptable emulsions, solutions, suspensions, syrups and elixirs containing inert diluents such as water or paraffin oil. These compositions can also comprise substances other than the diluents, for example wetting agents, sweeteners or flavourings.

The compositions for topical administration can, for example, be creams, ointments or lotions.

The compositions for ocular administration can be installations.

The compositions for intranasal administration can be pharmaceutically acceptable powders or solutions which are intended for drops or for sprays.

The compositions can also be aerosols. For use in the form of liquid aerosols, the compositions can be stable sterile solutions or solid compositions which are dissolved at the time of use in apyrogenic sterile water, serum or any other pharmaceutically acceptable vehicle. For use in the form of dry aerosols which are intended to be inhaled directly, the active principle is is finely divided and is combined with a solid, water-soluble vehicle or diluent having a particle size of from 30 to 80 μm, for example dextran, mannitol or lactose.

In human therapy, the products according to the invention can be useful in particular in the treatment of pain of traumatic, post-surgical, menstrual or cephalic origin, of facial vascular pain (cluster headache) and in the treatment of migraines. The novel isoindole derivatives are also useful in the treatment of inflammation in rheumatology, in the treatment of rheumatoid arthritis and in complaints caused by disruption of the immune system, in the treatment of inflammation in dermatology, such as psoriasis, herpes, urticaria, eczema, photodermatosis, burns and in dental or ocular inflammatory complaints, and in the field of lachrymal secretions; they are also useful in the treatment of painful and inflammatory spasmodic manifestations of the digestive system (ulcerative coliris, irritable bowel syndrome, Crohn's disease), the urinary tracts (urinary hyperreflexia, cystiris) and the respiratory tracts (asthma, bronchial hypersecretion, chronic bronchitis, rhinitis) and in antiemetic treatments. The products according to the invention can also find an application in the treatments of neurological diseases, Parkinson's disease, Alzheimer's disease, in the treatment inflammatory and/or autoimmune and/or demyelinating diseases of the central nervous system and/or the peripheral nervous system (multiple sclerosis, Guillain-Barré6 syndrome, encephalopathies whose origin is viral etc.), in neurological syndromes related to a plasmatic extravasation (oedema of the spinal cord, cerebral oedema, etc.), in relation to an attack on the blood-brain barrier or in any other spastic neurological syndrome (muscle-relaxing treatments). The products according to the invention can also be useful in the treatment of anxiety, psychosis, schizophrenia, Huntington's disease or else in the treatment of cardiovascular disorders such as hypotension. Another application can also be the treatment of gynaecological disorders, the treatment of disorders linked to poor growth regulation (dwarfism, hypothrophy secondary to chronic infant diseases, osteoporosis and the development of grafts).

The doses depend on the desired effect and on the duration of treatment. For an adult, they are generally between 0.25 and 1500 mg per day in graded doses.

Generally speaking, the doctor will determine the dosage which he considers to be the most appropriate depending on the age, weight and all the other factors specific to the subject to be treated.

The example which follows, given without any limitation being implied, illustrates a composition according to the invention.

Example A

The usual technique is used to prepare tablets of active product having the following composition:

| | |
|---|---|
| (3aS,4S,6S,7aR)-2-[(S)-2-amino-2-phenylacetyl]-6-cyanomethyl-4-(2-methoxyphenyl)perhydroisoindol-4-ol | 25 mg |
| starch | 83 mg |
| silica | 30 mg |
| magnesium stearate | 3 mg |

Example B

The usual technique is used to prepare tablets of active product having the following composition:

| | |
|---|---|
| (3aS,4S,6S,7aR)-6-cyanomethyl-4-(2-methoxyphenyl)-2-[(2-methoxyphenyl)acetyl]perhydroisoindol-4-ol | 25 mg |
| starch | 83 mg |
| silica | 30 mg |
| magnesium stearate | 3 mg |

Example C

The usual technique is used to prepare tablets of active product having the following composition:

| | |
|---|---|
| (3aS,4S,6S,7aR)-6-azidomethyl-4-(2-methoxyphenyl)-2-[(S)-2-(2-methoxyphenyl)propionyl]-perhydroisoindol-4-ol | 25 mg |
| starch | 83 mg |
| silica | 30 mg |
| magnesium stearate | 3 mg |

We claim:
1. A perhydroisoindole derivative of the formula:

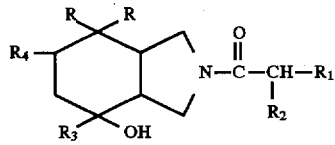

in which $R_1$ represents a phenyl radical which is unsubstituted or substituted with one or more halogen atoms or hydroxyl radicals, alkyl radicals which may be unsubstituted or substituted (with halogen atoms or with amino, alkylamino or dialkylamino radicals), alkyloxy or alkylthio radicals which may be unsubstituted or substituted {with hydroxyl, amino, alkylamino or dialkylamino radicals which are unsubstituted or substituted (with phenyl, hydroxyl or amino radicals), or dialkylamino radicals in which the alkyl moieties form, together with the nitrogen atom to which they are attached, a 5- to 6-membered heterocycle which can contain another heteroatom selected from oxygen, sulphur and nitrogen, which is unsubstituted or substituted with an alkyl, hydroxyl or hydroxyalkyl radical)}, or substituted with amino radicals or with alkylamino or dialkylamino radicals in which the alkyl moieties can form, together with the nitrogen atom to which they are attached, a heterocycle as defined above, or represents a cyclohexadienyl, naphthyl or indenyl radical or a saturated or unsaturated, mono- or polycyclic heterocyclic radical containing 5 to 9 carbon atoms and one or more heteroatoms selected from oxygen, nitrogen and sulphur, and unsubstituted or substituted with a halogen atom or with an alkyl or alkyloxy radical, $R_2$ represents a hydrogen or halogen atom or a hydroxyl, alkyl, amino, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl or acylamino radical, $R_3$ represents a phenyl radical which is unsubstituted or substituted in position 2 with an alkyl or alkyloxy radical containing 1 or 2 carbon atoms, a hydroxyl radical or a fluorine atom, or is disubstituted with trifluoromethyl radicals, and $R_4$ represents an alkyl radical containing 1 or 2 carbon atoms which is substituted with a halogen atom or with a cyano, azido or cyanamido radical, and R is identical or different and represents a hydrogen atom or an alkyl or phenyl radical, wherein the abovementioned acyl and alkyl radicals are (unless specified otherwise) straight or branched and contain 1 to 4 carbon atoms, wherein the perhydroisoindole derivative is in a racemic form, in its stereoisomeric forms of the structure:

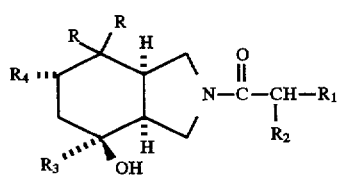

(Ia)

in its (R) or (S) forms on the chain —$CHR_1R_2$, or in the form of a mixture of two or more of these forms, or salts thereof.

2. The perhydroisoindole derivative according to claim 1, wherein $R_1$ is a saturated or unsaturated mono- or polycyclic heterocyclic radical selected from thienyl, furyl, pyridyl, dithiinyl, indolyl, isoindolyl, benzothienyl, thiazolyl, isothiazolyl, oxazolyl, imidazolyl, pyrrolyl, triazolyl, thiadiazolyl, quinolyl, isoquinolyl and naphthyridinyl.

3. A process for the preparation of a perhydroisoindole derivative according to claim 1, wherein an acid, or a reactive derivative of the acid, of formula:

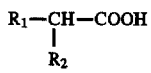

in which $R_1$ and $R_2$ are defined as in claim 1, is reacted with an isoindole derivative of formula:

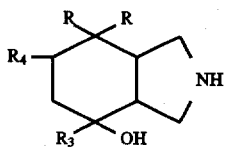

in which R, $R_3$, and $R_4$ are defined as in claim 1, then, when $R_4$ is an azidoalkyl radical, this radical is optionally converted into a cyanoaminoalkyl radical, the protecting radical (s) is(are) optionally eliminated, the stereoisomers are optionally separated, and the product obtained is optionally converted to a salt.

4. A process for the preparation of a perhydroisoindole derivative according to claim 1, wherein an alkali metal cyanide, sodium azide or an alkali metal halide is reacted with a perhydroisoindole derivative of formula:

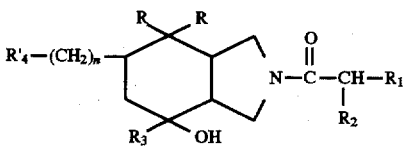

in which R, $R_1$, $R_2$ and $R_3$ are defined as in claim 1, $R'_4$ represents a sulphonyloxy radical and n represents 1 or 2, to obtain the derivative according to claim 1 in which $R_4$ is cyanoalkyl, azidoalkyl or haloalkyl, and the product obtained in which $R_4$ is azidoalkyl is optionally converted into a product according to claim 1 in which $R_4$ is cyanoaminoalkyl, or else the product obtained in which $R_4$ is haloalkyl is optionally converted into a product according to claim 1 in which $R_4$ is cyanoalkyl or azidoalkyl, the stereoisomers are optionally separated, and the product obtained is optionally converted to a salt.

5. A perhydroisoindole derivative of the formula:

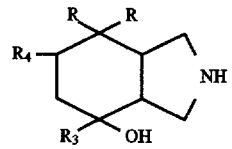

in which R, $R_3$, and $R_4$ are defined as in claim 1, in racemic form, in its stereoisomeric forms, or in the form of a mixture of two or more of these forms, or salts thereof.

6. A pharmaceutical composition comprising at least one perhydroisoindole derivative according to claim 1 and one or more pharmaceutically-acceptable carriers.

7. A pharmaceutical composition comprising at least one perhydroisoindole derivative according to claim 1 and at least one NK2 receptor antagonist.

8. A pharmaceutical composition comprising a perhydroisoindole derivative of claim 1 and a pharmaceutically-compatible product.

* * * * *